(12) United States Patent
Vorp et al.

(10) Patent No.: US 12,280,112 B2
(45) Date of Patent: Apr. 22, 2025

(54) MAGNETIC DELIVERY SYSTEM AND HYDROGEL FIXATIVE FOR THERAPEUTIC CELLS

(71) Applicants: University of Pittsburgh—Of the Commonwealth System of Higher Education, Pittsburgh, PA (US); Vanderbilt University, Nashville, TN (US)

(72) Inventors: David A. Vorp, Pittsburgh, PA (US); Aneesh Krishna Ramaswamy, Pittsburgh, PA (US); Justin Sol Weinbaum, Allison Park, PA (US); Kory James Blose, Pittsburgh, PA (US); Timothy Kwang-Joon Chung, Pittsburgh, PA (US); Trevor Kickliter, Allentown, PA (US); Yogev Baruch, Pittsburgh, PA (US); John A. Curci, Nashville, TN (US)

(73) Assignees: University of Pittsburgh—Of the Commonwealth System of Higher Education, Pittsburgh, PA (US); Vanderbilt University, Nashville, TN (US)

( * ) Notice: Subject to any disclaimer, the term of this patent is extended or adjusted under 35 U.S.C. 154(b) by 990 days.

(21) Appl. No.: 17/286,210

(22) PCT Filed: Oct. 18, 2019

(86) PCT No.: PCT/US2019/056976
§ 371 (c)(1),
(2) Date: Apr. 16, 2021

(87) PCT Pub. No.: WO2020/081957
PCT Pub. Date: Apr. 23, 2020

(65) Prior Publication Data
US 2021/0338816 A1    Nov. 4, 2021

Related U.S. Application Data

(60) Provisional application No. 62/747,767, filed on Oct. 19, 2018.

(51) Int. Cl.
*A61K 41/00* (2020.01)
*A61K 35/28* (2015.01)
(Continued)

(52) U.S. Cl.
CPC .............. *A61K 41/00* (2013.01); *A61K 35/28* (2013.01); *A61M 5/1407* (2013.01);
(Continued)

(58) Field of Classification Search
CPC ........ A61K 41/00; A61K 35/28; A61K 35/12; A61M 5/1407; A61M 25/0127;
(Continued)

(56) References Cited

U.S. PATENT DOCUMENTS 8,673,323 B2    3/2014   Thomopoulos et al.
2006/0041182 A1  2/2006   Forbes et al.
(Continued)

FOREIGN PATENT DOCUMENTS

WO    2014093581 A1    6/2014

OTHER PUBLICATIONS

Bensaïd et al., "A biodegradable fibrin scaffold for mesenchymal stem cell transplantation", Biomaterials, 2003, pp. 2497-2502, vol. 24.
(Continued)

*Primary Examiner* — Joel M Attey
*Assistant Examiner* — Alexandra Lalonde
(74) *Attorney, Agent, or Firm* — The Webb Law Firm

(57) ABSTRACT

A method of delivering cells to a target tissue is provided comprising depositing a hydrogel pre-gel comprising magnetic particle-loaded cells to the target tissue and, prior to or during gelation of the hydrogel, drawing the magnetic particle-loaded cells to the tissue with a magnetic field, followed by gelation of the hydrogel to lock the cells in place on the tissue. The cells may be mesenchymal stem cells, such as adipose-derived mesenchymal stem cells, and the target tissue may be adventitial tissue of an aneurysm in a blood vessel. Also provided are devices useful in the method.

15 Claims, 15 Drawing Sheets

(51) Int. Cl.
    *A61M 5/14*     (2006.01)
    *A61M 25/01*     (2006.01)
    *A61M 25/09*     (2006.01)
    *C12N 5/0775*     (2010.01)

(52) U.S. Cl.
    CPC .. *A61M 25/0127* (2013.01); *A61M 25/09041* (2013.01); *C12N 5/0667* (2013.01); *A61M 2202/09* (2013.01); *A61M 2205/0288* (2013.01)

(58) Field of Classification Search
    CPC ........ A61M 25/09041; A61M 2202/09; A61M 2205/0288; A61M 25/0158; A61M 2205/0272; A61M 2205/057; A61M 2205/8287; A61M 2202/0007; A61M 2202/0449; A61M 2202/0425; A61M 2202/10; A61M 2202/0437; A61M 2210/12; A61M 2210/127; A61M 2210/125; A61M 2037/0007; C12N 5/0667; C12N 5/0668; A61L 2300/64; A61L 24/0005; A61L 24/001; A61L 24/0015; A61L 24/0031; C12M 25/14; C12M 33/00
    See application file for complete search history.

(56) References Cited

U.S. PATENT DOCUMENTS

| | | | |
|---|---|---|---|
| 2008/0160085 | A1 | 7/2008 | Boland et al. |
| 2010/0028311 | A1 | 2/2010 | Motlagh et al. |
| 2010/0209398 | A1* | 8/2010 | Tankovich ............... A61P 25/28 424/93.7 |
| 2012/0214217 | A1* | 8/2012 | Grogan ................. C12N 5/0655 435/325 |
| 2012/0253102 | A1 | 10/2012 | Marban et al. |
| 2013/0261373 | A1 | 10/2013 | Pison et al. |
| 2015/0112299 | A1 | 4/2015 | Forbes et al. |
| 2015/0313995 | A1 | 11/2015 | Hung |
| 2018/0133401 | A1 | 5/2018 | Schwab et al. |
| 2019/0175495 | A1* | 6/2019 | Taylor ..................... A61L 27/52 |

OTHER PUBLICATIONS

Blose et al., "Periadventitial adipose-derived stem cell treatment halts elastase-induced abdominal aortic aneurysm progression", Regen Med., Nov. 2014, pp. 733-741, vol. 9:6.

Chung et al., "Magnetic field assisted localization of ADMSCs with iron nanoparticles", McGowan Retreat, 2018, 6 pages.

Consigny et al., "Use of Endothelial Cells Containing Superparamagnetic Microspheres to Improve Endothelial Cell Delivery to Arterial Surfaces after Angioplasty", JVIR, 1999, pp. 155-163, vol. 10.

Frese et al., "Adipose Tissue-Derived Stem Cells in Regenerative Medicine", Transfusion Medicine and Hemotherapy, 2016, pp. 268-274, vol. 43.

Hashizume et al., "Mesenchymal stem cells attenuate angiotensin II-induced aortic aneurysm growth in apolipoprotein E-deficient mice", Journal of Vascular Surgery, Dec. 2011, pp. 1743-1752, vol. 54.

Hou et al., "In Vitro Evaluation of a Fibrin Gel Antibiotic Delivery System Containing Mesenchymal Stem Cells and Vancomycin Alginate Beads for Treating Bone Infections and Facilitating Bone Formation", Tissue Engineering: Part A, 2008, pp. 1173-1182, vol. 14:7.

Kickliter et al., "Adventitial Delivery of Adipose-Derived Mesenchymal Stem Cells to Large Animal Aortas", University of Pittsburgh Presentation, 2018, 1 page.

Kontopodis et al., "The-Not So-Solid 5.5 cm Threshold for Abdominal Aortic Aneurysm Repair: Facts, Misinterpretations, and Future Directions", Frontiers in Surgery, Jan. 2016, 6 pages, vol. 3.

Kurosawa et al., "Current Status of Medical Treatment for Abdominal Aortic Aneurysm", Circulation Journal, Dec. 2013, pp. 2860-2866, vol. 77.

Ludwig et al., "Structural properties of magnetic nanoparticles determine their heating behavior—an estimation of the in vivo heating potential", Nanoscale Research Letters, 2014, 10 pages, vol. 9.

Nazli et al., "RGDS-functionalized polyethylene glycol hydrogel-coated magnetic iron oxide nanoparticles enhance specific intracellular uptake by Hela cells", International Journal of Nanomedicine, 2012, pp. 1903-1920, vol. 7.

Palumbo et al., "Methods of Isolation, Characterization and Expansion of Human Adipose-Derived Stem Cells (ASCs): An Overview", International Journal of Molecular Sciences, 2018, 13 pages, vol. 19.

Pislaru et al., "Magnetically Targeted Endothelial Cell Localization in Stented Vessels", Journal of the American College of Cardiology, 2006, pp. 1839-1845, vol. 48:9.

Schlösser et al., "Mortality After Elective Abdominal Aortic Aneurysm Repair", Annals of Surgery, Jan. 2010, pp. 158-164, vol. 251:1.

Sharma et al., "Experimental abdominal aortic aneurysm formation is mediated by IL-17 and attenuated by mesenchymal stem cell treatment", Circulation, Sep. 2012, pp. S38-S45, vol. 126.

Siepe et al., "Stem cells used for cardiovascular tissue engineering", European Journal of Cardio-Thoracic Surgery, 2008, pp. 242-247, vol. 34.

Tefft et al., "Magnetizable stent-grafts enable endothelial cell capture", Journal of Magnetism and Magnetic Materials, 2017, pp. 100-104, vol. 427.

Turnbull et al., "Aortic Implantation of Mesenchymal Stem Cells after Aneurysm Injury in a Porcine Model", J Surg Res., Sep. 2011, pp. e179-e188, vol. 170:1.

\* cited by examiner

Rat 03

Rat 04

MAGNETIC DELIVERY SYSTEM AND HYDROGEL FIXATIVE FOR THERAPEUTIC CELLS

CROSS REFERENCE TO RELATED APPLICATIONS

This application is the United States national phase of International Application No. PCT/US2019/056976 filed Oct. 18, 2019, and claims the benefit of United States Provisional Patent Application No. 62/747,767, filed Oct. 19, 2018, the disclosures of which are hereby incorporated by reference in their entirety.

STATEMENT REGARDING FEDERAL FUNDING

This invention was made with government support under Grant Nos. HL129066; HL076124; EB000392; HL086418; HL129066 and AG037120 awarded by the National Institutes of Health. The government has certain rights in the invention.

Stem cell therapy has been of great interest in treating a variety of diseases. However, many of the targeted sites for delivery of cells to treat these diseases are internal and therefore difficult to reach. Currently-available technologies for therapeutic cell delivery to diseased areas include biodegradable scaffolds, injections to the blood stream and stem-cell patches. However, none of these technologies can accurately deliver cells to internal locations and fix them in place where they are needed.

Rupture of an abdominal aortic aneurysm (AAA) is a leading cause of death in the United States. To avoid this outcome, patients typically undergo endovascular repair once their aneurysm grows beyond 5.0-5.5 cm in diameter. However, because many AAAs above this diameter go unruptured and surgical repair of AAAs below this diameter generally fails to improve survival rates, this method often proves unnecessary. This necessitates new therapies for AAA that overcome these shortcomings. Adipose-derived mesenchymal stem cells (ADMSCs) have been shown to be effective at halting AAA expansion (Blose, K. J., et al. "Periadventitial adipose-derived stem cell treatment halts elastase-induced abdominal aortic aneurysm progression" (2014) Regen Med 9(6):733-41). However, a method to effectively target ADMSCs to the aorta has yet to be developed or tested in large animals.

SUMMARY

A method of delivering a cell to a target tissue is provided. The method comprises mixing cells comprising internalized magnetic particles with a hydrogel pre-gel composition; depositing the pre-gel composition comprising the cells at a site on or adjacent to a tissue, under conditions suitable for gelation of the pre-gel composition such that the pre-gel composition forms a hydrogel at the site; and prior or during gelation of the hydrogel, applying a magnetic field to the cells in the deposited pre-gel to draw the cells to the target tissue.

In another aspect, a method of treating an aneurysm in a patient is provided. The method comprises delivering mesenchymal stem cells (MSCs) to adventitia on or about the aneurysm by depositing a pre-gel composition comprising cells comprising internalized magnetic particles at a site on or adjacent to a tissue, under conditions suitable for gelation of the pre-gel composition such that the pre-gel composition forms a hydrogel at the site; and prior or during gelation of the hydrogel, applying a magnetic field to the cells in the deposited pre-gel to draw the cells to the target tissue.

In another aspect, a device is provided comprising: a first reservoir comprising cells comprising internalized magnetic particles; one or more additional reservoirs comprising a hydrogel pre-gel composition or ingredients, when mixed, form a hydrogel pre-gel composition; a mixing chamber having an outlet, configured to mix the contents of the first reservoir with contents of the one or more additional reservoirs, fluidly-connected in a closed fluid path to the first reservoir and the one or more additional reservoirs; one or more pumps or plungers configured to deliver liquid from the reservoirs, through the mixing chamber, and through the outlet of the mixing chamber.

In another aspect, a catheter device is provided, comprising a sheath, a guide wire within the sheath, and a diametric magnet of at least 1000 or at least 2000 gauss, such as 4000 gauss, attached to a distal end of the guide wire and having a diameter less than an inside diameter of the sheath, so that the magnet can be deployed beyond a distal end of the sheath and retracted within the sheath for catheter removal.

The following numbered clauses illustrate various aspects or embodiments of the invention.

Clause 1. A method of delivering a cell to a target tissue, comprising:
mixing cells comprising internalized magnetic particles with a hydrogel pre-gel composition;
depositing the pre-gel composition comprising the cells at a site on or adjacent to a tissue, under conditions suitable for gelation of the pre-gel composition such that the pre-gel composition forms a hydrogel at the site; and
prior or during gelation of the hydrogel, applying a magnetic field to the cells in the deposited pre-gel to draw the cells to the target tissue.

Clause 2. The method of clause 1, wherein the target tissue is a wound in a patient.

Clause 3. The method of clause 1, wherein the target tissue is blood vessel tissue.

Clause 4. The method of any one of clauses 1-3, wherein the pre-gel composition comprises a thermoresponsive polymer composition and forms a hydrogel at 37° C.

Clause 5. The method of any one of clauses 1-3, wherein one or more compounds or compositions in the pre-gel composition undergoes a chemical reaction to produce the hydrogel.

Clause 6. The method of clause 5, wherein the pre-gel composition comprises thrombin and fibrinogen.

Clause 7. The method of clause 6, wherein the pre-gel composition comprises from 0.1 mg/mL to 15 mg/mL fibrinogen or from 1 mg/mL to 12 mg/mL fibrinogen, such as 3 mg/mL or 10 mg/mL fibrinogen.

Clause 8. The method of any one of clauses 1-7, wherein the cell is a pluripotent cell, a stem cell, a multipotent cell, or a progenitor cell.

Clause 9. The method of any one of clauses 1-7, wherein the cell is a mesenchymal stem cell.

Clause 10. The method of any one of clauses 1-7, wherein the cell is an adipose-derived mesenchymal stem cell.

Clause 11. The method of any one of clauses 1-10, wherein the magnetic particle is a ferromagnetic nanoparticle having a diameter ranging from 1 nm to 500 nm, from 50 nm to 400 nm, 50 nm, 100 nm, 150 nm, 175 nm, or 200 nm.

Clause 12. The method of any one of clauses 1-11, wherein the magnetic particle is coated with a polysaccharide or poly(ethylene glycol).

Clause 13. The method of any one of clauses 1-12, further comprising adding the magnetic particles to cell culture media comprising cells and culturing the cells with the magnetic particles to produce the cells comprising internalized magnetic particles.

Clause 14. The method of any one of clauses 1-13, wherein the target tissue is blood vessel adventitia.

Clause 15. The method of clause 14, wherein the adventitia is blood vessel adventitia at a site of an aneurysm.

Clause 16. The method of clause 14, wherein the blood vessel adventitia is arterial.

Clause 17. The method of clause 14, wherein the blood vessel adventitia is aortic adventitia.

Clause 18. The method of clause 17, wherein the blood vessel adventitia is adventitia on or about an aortic aneurysm, such as an abdominal aortic aneurysm.

Clause 19. The method of any one of clauses 15-18, wherein the pre-gel composition comprising the cells is deposited peri-adventitially and the cells are drawn by the magnet to the adventitia.

Clause 20. The method of any one of clauses 15-18, wherein the magnetic field is produced by a diametric magnet that is placed within the blood vessel.

Clause 21. The method of any one of clauses 1-20, wherein the cell and/or the target tissue is human.

Clause 22. A method of treating an aneurysm in a patient, comprising delivering mesenchymal stem cells (MSCs) to adventitia on or about the aneurysm by depositing a pre-gel composition comprising MSCs comprising internalized magnetic particles at a site on or adjacent to a tissue, under conditions suitable for gelation of the pre-gel composition such that the pre-gel composition forms a hydrogel at the site; and prior or during gelation of the hydrogel, applying a magnetic field to the cells in the deposited pre-gel to draw the cells to the target tissue.

Clause 23. The method of clause 22, wherein the MSCs are adipose-derived mesenchymal stem cells.

Clause 24. The method of clause 22 or 23, wherein the aneurysm is an aortic aneurysm.

Clause 25. The method of clause 24, wherein the aneurysm is an abdominal aortic aneurysm.

Clause 26. The method of any one of clauses 22-25, wherein the patient is human.

Clause 27. The method of any one of clauses 22-26, further comprising, prior to depositing the pre-gel composition comprising MSCs comprising internalized magnetic particles at a site on or adjacent to a tissue, mixing MSCs comprising internalized magnetic particles with a hydrogel pre-gel composition to produce the pre-gel composition comprising MSCs comprising internalized magnetic particles.

Clause 28. The method of any one of clauses 22-27, wherein the pre-gel comprised fibrinogen and thrombin.

Clause 29. A device comprising:
 a first reservoir comprising cells comprising internalized magnetic particles;
 one or more additional reservoirs comprising a hydrogel pre-gel composition or ingredients, when mixed, form a hydrogel pre-gel composition;
 a mixing chamber having an outlet, configured to mix the contents of the first reservoir with contents of the one or more additional reservoirs, fluidly-connected in a closed fluid path to the first reservoir and the one or more additional reservoirs; and
 one or more pumps or plungers configured to deliver liquid from the reservoirs, through the mixing chamber, and through the outlet of the mixing chamber.

Clause 30. The device of clause 29, wherein the cells comprising internalized magnetic particles comprise precursor cells or stem cells comprising internalized magnetic particles.

Clause 31. The device of clause 30, wherein the cells are mesenchymal stem cells, such as adipose-derived mesenchymal stem cells.

Clause 32. The device of any one of clauses 29-31, wherein contents of the reservoirs are delivered to the mixing chamber by one or more pumps.

Clause 33. The device of any one of clauses 29-31, wherein the reservoirs are syringes having pistons.

Clause 34. The device of any one of clauses 29-33, comprising at least two additional reservoirs, with a first additional reservoir comprising thrombin and a second additional reservoir comprising fibrinogen.

Clause 35. A catheter comprising a sheath, a guide wire within the sheath, and a diametric magnet of at least 1000 or at least 2000 gauss, such as 4000 gauss, attached to a distal end of the guide wire and having a diameter less than an inside diameter of the sheath, so that the magnet can be deployed beyond a distal end of the sheath and retracted within the sheath for catheter removal.

BRIEF DESCRIPTION OF THE DRAWINGS

FIG. 3A has no guide pins, while FIG. 3B includes guide pins.

DETAILED DESCRIPTION

Figure 1:
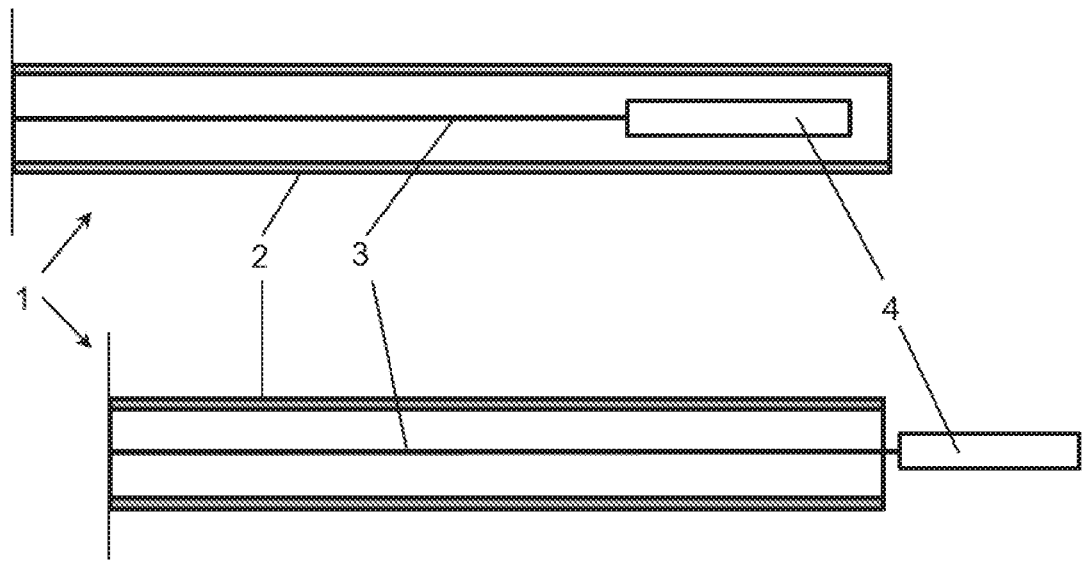
FIG. 1 provides a cross-sectional, schematic view of a catheter device for use in deploying a magnet in a blood vessel, as described herein, with the magnet sheathed (top) and deployed (bottom).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the singular form of "a", "an", and "the" include plural referents unless the context clearly dictates otherwise.

As used herein, the terms "upper", "lower", "right", "left", "vertical", "horizontal", "top", "bottom", "lateral", "longitudinal", and derivatives thereof, shall relate to the invention as it is oriented in the drawing figures. The term "proximal" refers to a portion of a structure nearest to the center of the structure or to a point of attachment or actuation of the structure. For example, a "proximal portion" of a syringe is the portion of the syringe configured to be grasped by a user. The term "distal" refers to a portion of a structure farthest away from the center or from the point of attachment or actuation of the structure (e.g., the portion of the structure opposite from the proximal portion). For example, a "distal portion" of a syringe is the end of the syringe including the needle, nozzle, or mixing chamber. However, it is to be understood that the invention may assume various alternative variations, except where expressly specified to the contrary. It is also to be understood that the specific devices illustrated in the attached drawings, and described in the following specification, are simply exemplary embodiments of aspects or embodiments of the invention.

As used herein, the "treatment" or "treating" of a condition, wound, or defect means administration to a patient by any suitable dosage regimen, procedure and/or administration route of a composition, device, or structure with the object of achieving a desirable clinical/medical end-point, including repair or improvement of a physical or biological property of a blood vessel, as in treatment of an aneurysm, such as an aortic aneurysm, such as an abdominal aortic aneurysm or treatment of a wound.

As used herein, the term "patient" or "subject" refers to members of the animal kingdom including but not limited to human beings and "mammal" refers to all mammals, including, but not limited to human beings.

As used herein, the term "polymer composition" is a composition comprising one or more polymers. As a class, "polymers" includes, without limitation, homopolymers, heteropolymers, co-polymers, block polymers, block co-polymers and can be both natural and/or synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups/moieties are missing and/or modified when incorporated into the polymer backbone. A polymer is said to comprise a specific type of linkage if that linkage is present in the polymer.

By "biodegradable" or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions for polymers include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize treatment.

As used herein, the terms "therapeutic agent" and "therapeutic agents" refer to any composition(s), such as drug(s) or active agent(s) having a preventative or therapeutic effect, including and without limitation, antibiotics, peptides, hormones, organic molecules, vitamins, supplements, factors, proteins and chemoattractants. A "therapy" or "treatment" refers to administration of a therapeutic composition, such as the compositions described herein, in amounts effective to reach an acceptable end point, e.g., a clinical end point, such as the repair of a heart valve.

As used herein, the terms "cell" and "cells" refer to any types of cells from any animal, such as, without limitation, rat, mice, monkey, and human. For example, and without limitation, cells can be progenitor cells, such as stem cells, or differentiated cells, such as endothelial cells, or smooth muscle cells. In certain embodiments, cells for medical procedures can be obtained from the patient for autologous procedures or from other donors for allogeneic procedures.

Provided herein is a method of delivering a therapeutic cell of interest to a target tissue. The method comprises loading a therapeutic cell of interest with MNPs, and mixing these cells with a gelation solution or pre-gel for a hydrogel, such as a biodegradable hydrogel. The pre-gel solution comprising MNP-loaded cells is then injected to a location of interest near or adjacent to the target tissue, in conjunction with a magnet placed (externally or otherwise non-invasively or minimally-invasively) to attract the MNP-loaded cells within the pre-gel solution to the target tissue, where the pre-gel can set, or gel, fixing the cells in place to perform their therapeutic function. As described in the examples below, studies directed at the application of this method to treatment of abdominal aortic aneurysm have demonstrated the ability to magnetically localize therapeutic cells next to the aorta, encapsulated within a hydrogel.

As shown below, the method described herein effectively delivers a dose of stem cells to the peri-adventitia, or outside, of an aneurysm and then encourage stem cell migration into the wall of the vessel. Stem cells loaded with MNPs are delivered in a hydrogel pre-gel composition or solution to trap the cells in place, after drawing the cells to a target tissue with a magnet. The stem cells used in this system could be from any origin. The MNPs used in this method may vary in size with the restriction being that a cell is able to engulf the particle. Any metal could be used provided it is magnetic, diamagnetic, or paramagnetic and non-toxic to the stem cells and host cells. The hydrogel may be a hydrogel that is capable of being pushed through a needle as small as 30 gauge and is non-toxic to the stem cells and host cells. Additional proteins (such as growth factors) or peptides could be added to the hydrogel.

The magnet may be a magnetic material or an electromagnet that is placed either in the lumen of the aneurysm, at another location internal to the patient, or outside of the patient. The magnet is arranged so that the magnetic field produced by the magnet draws the magnetic particle-loaded cells to the target tissue, e.g., adjacent to the target tissue, onto the target tissue, and/or into the target tissue. The hydrogel contains the stem cells at the site of injection. The site for deposition of the pre-gel may be found via ultrasonic guidance. The stem cells are encouraged to migrate from the hydrogel pre-gel to the aneurysmal tissue due to magnetic forces between the MNPs, which were engulfed by the stem cells prior to mixture with the hydrogel, and a magnet placed either in the lumen of the aneurysm, at another site in the patient's body, or on the outside of the patient.

The described method of delivering cells to a tissue provides a new therapy for patients with small aneurysms and an alternative therapy for patients with large aneurysms. The benefits are a means of delivering a localized therapy to aneurysmal tissue through minimally invasive surgical techniques. The method may include delivery of a cellular therapeutic to the outside of an aneurysm and uses a hydrogel assist in localizing the therapy, combined with magnetic homing, used to encourage cellular migration to the diseased tissue. Delivering the therapeutic locally to the outside of the aneurysm is advantageous over lumenal delivery (e.g., intravascular injections) of therapeutics due to the presence of physical barrier often found in aneurysmal arteries called the intraluminal thrombis. Lumenal delivery of therapeutics also suffers from poor vasa vasorum function in aneurysmal arteries and delivery inefficiency to the targeted site.

A hydrogel pre-gel composition is used to deliver MNP-loaded cells to a tissue target and to gel in situ to hold the MNP-loaded cells in place once they are drawn to the target tissue by a magnetic field. A hydrogel is a water-swellable polymer-containing composition with water or an aqueous solution retained within its structure. A hydrogel is not dissolved in, or is incompletely dissolved in, water or in its aqueous component. A hydrogel pre-gel composition is a composition that will form a hydrogel under specific conditions, such as at 37° C. through chemical modification and/or through physical transformation. The hydrogel may be formed from a pre-gel by physical transformation. Where the transformation is temperature-dependent, the polymer composition may be referred to as a thermoresponsive hydrogel. A thermoresponsive hydrogel composition comprises a polymer composition in an aqueous solution that, in context of the present disclosure, forms a gel at 37° C., but does not form a gel, or forms a gel significantly more slowly, at a temperature below 37° C., 35° C., 30° C., 25° C., 20° C., 15° C., or 10° C. This gelation process in transforming from a pre-gel at a first temperature to a hydrogel at a second temperature is a physical, phase-shift or solubility transformation, which may be contrasted with the formation of a hydrogel by chemical modification of its constituents or precursors as in polymerization reactions or cross-linking reactions, for example the formation of a fibrin gel (e.g., a fibrin glue) from a mixture of fibrinogen and thrombin, or other mechanisms, such as pH, light, or interaction with other chemical compositions. For example, a thermoresponsive polymer composition, e.g. prior to delivery to a patient, can be maintained at a temperature below 37° C., e.g., 25° C., 20° C., 15° C., 10° C. or 4° C., or on ice, without gel formation, and in this physical state is referred to as a pre-gel, and when the gel is warmed to 37° C., it forms a hydrogel. Such thermoresponsive gels also may be referred to as having a lower critical solution temperature (LOST) below 37° C., 35° C., 30° C., 25° C., 20° C., 15° C., or 10° C., below which temperature the thermoresponsive gel polymer composition is miscible in its solvent—again, referred to as a pre-gel—and above which temperature the pre-gel will gel. In aspects a pre-gel solution, including cells, can be delivered to a patient or tissue through a 16g (16 gauge), 19g, 26g, or 30g needle. Aqueous solutions useful in hydrogels and hydrogel pre-gel compositions described herein may be pharmaceutically-acceptable, and not damaging or toxic to any substantial extent to cells to be embedded in the hydrogel, to the tissue to be targeted, or, more generally, in their use for in vivo methods, and include water, normal saline, phosphate-buffered saline or other pharmaceutically-acceptable aqueous carriers.

In other aspects, a polymer composition is not necessarily thermoresponsive, but a pre-gel composition therefore may comprise all ingredients necessary for the formation of a hydrogel, and which over time, due to chemical reaction or physical restructuring, will form a hydrogel under suitable reaction conditions. In use, and in the context of the present disclosure a pre-gel may be mixed immediately before use and delivered with ferromagnetic particle-laden cells to a tissue prior to complete formation of the hydrogel, and where the process of gelling (or gelation) occurs in situ on or adjacent to the tissue. Prior to gelation of the hydrogel, MNP-loaded cells may be drawn with a magnet to a target tissue, and locked into place once the gel is formed. As with thermoresponsive polymers a pre-gel composition is a composition that is not a completely-formed hydrogel, and which can be delivered to a patient or tissue through a needle, such as a 16g, 19g, 26g, or 30g needle.

The hydrogel may be a fibrin glue, which is a composition comprising as a pre-gel, fibrinogen and thrombin, which will form a fibrin matrix upon gelation. Fibrinogen and thrombin both are broadly-available commercially, and their use in preparation of fibrin glues and hydrogels is well-studied. The fibrinogen may be human fibrinogen obtained, e.g., from human plasma. The thrombin catalyzes the reaction, and can be from any suitable source, such as bovine thrombin. As described in the examples below, the density of the fibrin network will be dictated, at least in part, by the concentration of fibrinogen in the pre-gel. Amounts or concentration of fibrinogen in the pre-gel, for mixing with cells, range from 0.1 mg/mL to 15 mg/mL fibrinogen, from 1 mg/mL to 12 mg/mL fibrinogen, e.g., 3 mg/mL or 10 mg/mL fibrinogen. The amount of thrombin, fibrinogen, and/or calcium (a cofactor for thrombin) may be adjusted to regulate the rate of hydrogel formation. The rate of hydrogel formation is preferably slow enough to ensure timely and effective movement of magnetic particle-loaded cells to a tissue in a provided magnetic field, but fast enough to timely stabilize the area of deposition during or soon after application of the magnetic field and drawing of the cells to the target tissue.

Other hydrogel compositions may be used in the methods described herein, such as suitable biocompatible, biodegradable polymers and (co)polymers. Non-limiting examples of a bioerodible polymer useful in the method and device described herein, include: polyurethane, polyester, polyester-containing, polyanhydride, polyanhydride-containing, polyorthoester, and polyorthoester-containing copolymers. The polyester or polyester-containing copolymer may be a poly(lactic-co-glycolic) acid (PLGA) copolymer. The bioerodible polymer may be selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

Magnetic particle-laden cells, e.g., "nanoparticle-loaded cells" comprise internalized magnetic particles, such as ferromagnetic nanoparticles, internal to their cell membrane, e.g., within their cytoplasm or an organelle or compartment thereof, such as a vesicle. Loading of cells with the nanoparticles may be accomplished by culturing the cells in the presence of the MNPs. MNPs are a class of nanoparticle that can be manipulated using magnetic fields. MNPs typically are ferromagnetic particles or ferrite nanoparticles, comprising iron oxide, such as magnetite or maghemite. The particles may be single-core or multi-core. Commercially-available magnetic particles, and those useful for is in biological systems and methods such as those described herein, may be coated, for example, and without limitation, with hydrophilic polymers, such as polysaccharides (e.g., starch, dextrin, or dextran), poly(ethylene glycol) ("PEG" or "PEGylated"), or polyacrylates which protect them against aggregation by foreign ions. The particle coatings may include functional groups such as hydroxyl, amine, or carboxyl groups. In one aspect, the magnetic particle is covered with starch or dextrin.

The magnetic particles, e.g. MNPs, have a size ranging from 1 nm to 500 nm, or from 50 nm to 400 nm, including any increments therebetween, such as 50 nm, 100 nm, 150 nm, 175 nm, or 200 nm, and may be measured, statistically classified, and/or physically classified (sorted) by any acceptable method. In one aspect, particle size is determined by analyzing hydrodynamic diameter. Determination of MNP core size and shape may be performed by high-resolution transmission electron microscopy (HRTEM). Hydrodynamic diameters may be obtained via dynamic light scattering (DLS) using a Zetasizer Nano ZS (Malvern Instruments GmbH, Herrenberg, Germany) with a measurement angle of 173° backscatter (see, e.g., Ludwig R, Stapf M, Dutz S, Müller R, Teichgräber U, Hilger I. Structural properties of magnetic nanoparticles determine their heating behavior—an estimation of the in vivo heating potential. *Nanoscale Res Lett.* 2014; 9(1):602. Published 2014 Nov. 5. doi:10.1186/1556-276X-9-602). The magnetic particles may be magnetic, diamagnetic, or paramagnetic.

Non-limiting examples of MNPs useful in the methods described herein, include fluidMAG-nanoparticles (chemicell, GmbH, Berlin, Germany), including are ferrofluids consisting of an aqueous dispersion of magnetic iron oxides with diameters of 50 nm, 100 nm and 200 nm.

The hydrogel compositions may also include additional components, such as an active agent, such as, without limitation, one or more of an antiseptic, an antibiotic, an analgesic, an anesthetic, a chemotherapeutic agent, an anti-inflammatory agent, a metabolite, a cytokine, a chemoattractant, a hormone, a steroid, a protein, or a nucleic acid. Active agents that may be incorporated into the hydrogel include, without limitation, anti-inflammatories, such as, without limitation, nitro-fatty acids NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); or antibiotics. Other drugs, active agents, or compositions that may promote wound healing and/or tissue regeneration may also be included in the pre-gel and hydrogel.

Pharmaceutically acceptable salts or prodrugs of any active agent (e.g., therapeutic agent or drug), bound to or otherwise combined with, or incorporated into the composition according to any aspect herein, may also be employed. Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acid. Suitable pharmaceutically acceptable basic salts include without limitation, ammonium salts, alkali metal salts (such as sodium and potassium salts), alkaline earth metal salts (such as Mg and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

Any useful cytokine or chemoattractant can be mixed into, mixed with, or otherwise combined with the hydrogel. For example, and without limitation, useful components include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts.

In the methods described herein MNP-loaded cells are deposited in a hydrogel pre-gel composition. Non-limiting examples of useful cells include: stem cells, progenitor cells, and differentiated cells; recombinant cells; mesenchymal progenitor or stem cells; or endothelial cells; including, without limitation, adipose-derived, placental-derived, umbilical cord-derived, bone marrow derived, circulating (blood)-derived, or skeletal muscle-derived progenitor cells or stem cells. Further examples of potentially useful cells include: venous and arterial (e.g. radial artery) endothelial cells, endothelial progenitor cells (EPC), mesenchymal stem cells derived EC isolated from a bone marrow biopsy or human umbilical cord-derived fibroblasts, and endothelial progenitor cells (See, e.g., Siepe et al., Stem Cells Used for Cardiovascular Tissue Engineering, European Journal of Cardio-thoracic Surgery 34 (2008) 242-247). In one aspect, the cells are autologous with respect to the patient to be treated. In another aspect, the cells are allogeneic with respect to the patient to be treated.

Multipotent mesenchymal stem cells can be readily isolated from bone marrow or adipose tissue. Adipose-derived mesenchymal stem cells are an excellent source of MSCs for use in the method described herein, e.g. for periadventitial delivery of stem cells for treatment of an aneurysm. ADSCs can be harvested using minimal invasive procedures with little risk and discomfort compared to bone marrow-derived stem cells. They can be obtained in large quantities with minimally invasive procedures (See, e.g., Frese L, et al. Adipose Tissue-Derived Stem Cells in Regenerative Medicine. *Transfus Med Hemother.* 2016; 43(4):268-74 and Palumbo P, et al. Methods of Isolation, Characterization and Expansion of Human Adipose-Derived Stem Cells (ASCs): An Overview. *Int J Mol Sci.* 2018; 19(7):1897. Published 2018 Jun. 28. doi:10.3390/ijms19071897) e.g., by collagenase digestion of lipoaspirate followed by differential centrifugation. So ADSCs are a great autologous resource. Autologous ADSCs can be retrieved from either liposuction aspirates or subcutaneous adipose tissue fragments and are easily expanded in vitro. For non-high-risk patients, stocked frozen ADSCs can be delivered and thawed for allogeneic transplantation.

A magnet is a material or object that produces a magnetic field. The magnet may be a permanent magnet or an electromagnet. To produce a broader magnetic field a diametric magnet may be employed. In use for treatment of a patient, a magnet may be provided external to a patient or may be deployed internally in a patient when drawing the MNP-loaded cells to a tissue. The magnet may be deployed in a blood vessel, such as an abdominal aorta, for drawing MNP-loaded calls to that blood vessel. The magnet may be deployed internally in a patient via any suitable route, e.g. using a catheter device.

A catheter device for use in the methods described herein is provided. An example of a catheter device 1 for placement of a magnet in a blood vessel is shown schematically in FIG. 1 and comprises a sheath 2 (showing only a distal end of the catheter), a guide wire 3, and a magnet 4, such as a diametric magnet. The catheter device 1 is depicted with the magnet 4 sheathed (top) and with the magnet 4 deployed by manipulation of the guide wire and with the magnet deployed therein, for delivery through a blood vessel of the patient, such as the classical femoral artery route. Useful materials and structures for the sheath 2 and the guide wire 3, are broadly-known.

The MNP-loaded cells may be delivered by the methods described herein for any suitable purpose, such as for therapeutic uses or regenerative purposes. The method provided herein may be used to deliver stem cells, e.g., MSCs, such as ADMSCs, to a tissue for repair of the tissue. For example, a method of treating a wound, such as a traumatic wound or a surgical wound, is provided, comprising delivering MNP-loaded cells, e.g., MSCs, such as ADMSCs, to the site of the wound according to the method provided herein.

A method of treating an aneurysm is provided, comprising delivering MNP-loaded cells, e.g., MSCs, such as ADMSCs, to the site of the aneurysm, e.g. to adventitia of a blood vessel at the site of an aneurysm. The pre-gel composition comprising MNP-loaded stem cells is deposited on the adventitial side of an aneurysm in a blood vessel, and a magnetic field is applied to draw the MNP-loaded stem cells to the adventitia. A sponge or mold (form) may be used to assist in localization of the pre-gel composition on the blood vessel and to hold the pre-gel in place prior to gelation to form the hydrogel. Where accessible, such as in the abdominal aorta, aorta, or carotid artery, for example and without limitation, a magnet may be deployed via catheter to the lumen of the blood vessel at the site of the aneurysm (see FIG. 1). Delivery of the MNP-loaded cells may be monitored by ultrasound of x-ray, and radiopaque markers may be utilized to assist in localization at the site of the aneurysm. Any suitable amount of the pre-gel composition comprising the MNP-loaded cells may be deposited peri-adventitially, depending, among other factors, on the size, severity, and location of the aneurysm, as well as the concentration of MNP-loaded cells in the pre-gel composition.

Figure 2:
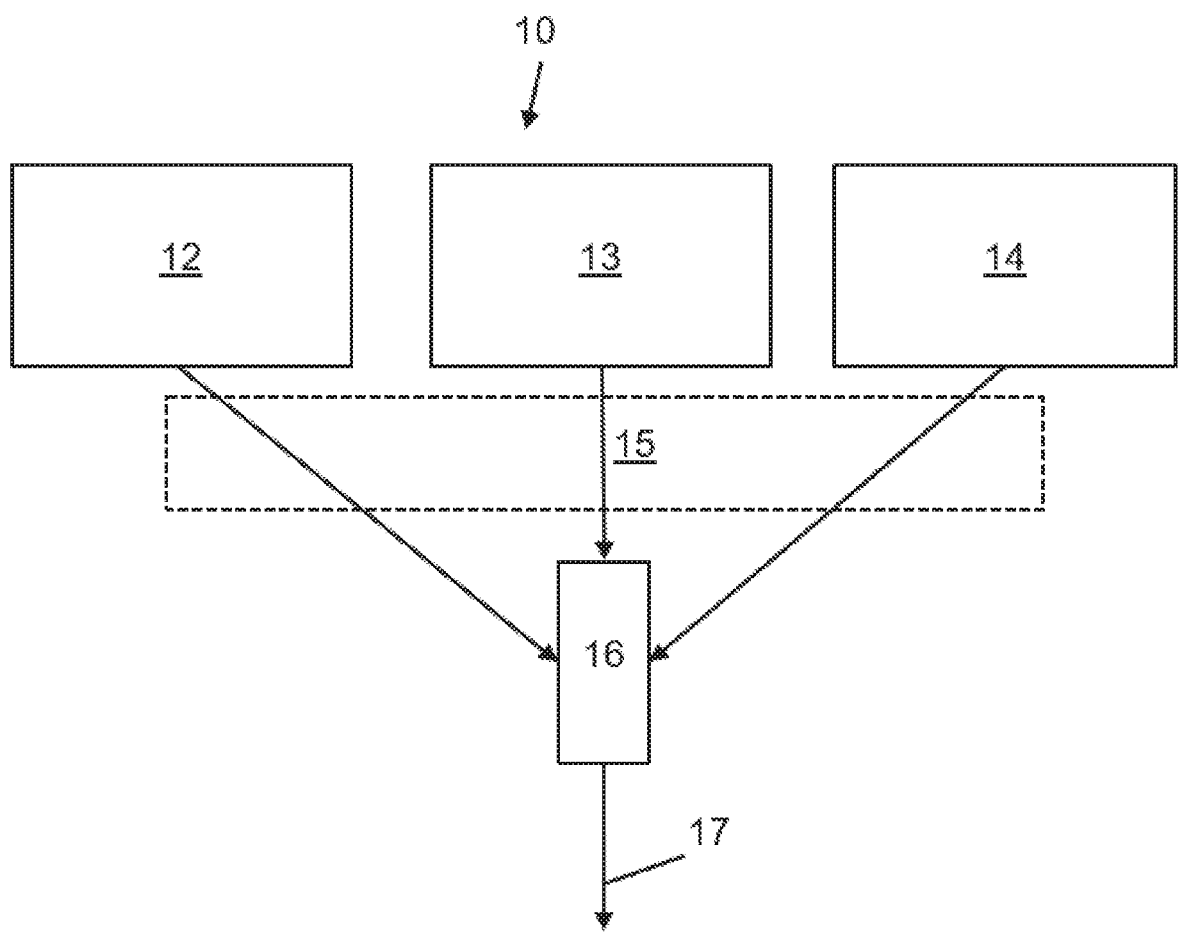
FIG. 2 depicts schematically liquid storage, transfer, and mixing in a device for delivering a pre-gel composition comprising magnetic nanoparticle (MNP)-loaded cells.

FIG. 2 provides a schematic diagram of a device 10 for mixing MNP-loaded cells and a hydrogel pre-gel composition. The system 10 comprises three reservoirs 12, 13, 14. Reservoir 12 comprises a solution comprising MNP-loaded cells. Reservoir 13 comprises a fibrinogen solution. Reservoir 14 comprises a thrombin solution. The reservoirs may be a medical syringe comprising a syringe body and plunger (see, e.g., FIGS. 3A and 3B). A fluid pumping mechanism 15 is provided, which may comprise a pump (e.g., a peristaltic or infusion pump), valves, or a manual or automatic plunger system for transferring liquids from the reservoirs 12, 13, 14 to a mixing chamber 16 in which the liquids transferred from reservoirs 12, 13, 14 are mixed to produce a pre-gel composition. Reservoirs 12, 13, 14 are fluidly-connected to the mixing chamber 16 by tubing, a manifold, or any other suitable passageways for liquid transfer, e.g. under pressure. Outlet 17 from the mixing chamber is provided to deposit mixed pre-gel composition to a tissue, and may comprise additional pumps, valves, tubes, cannulae, catheters, needles, etc. The fluid path including reservoirs 12, 13, 14, pumping mechanism 15, mixing chamber 16, and outlet 17 may form a closed and/or contiguous fluid path. Although reservoirs 13 and 14 are said to comprise fibrinogen and thrombin solutions, they may comprise any hydrogel-forming compositions, and in the case of using a thermoresponsive polymer for the hydrogel, reservoir 14 may be omitted, with reservoir 13 comprising a pre-gel composition for a thermoresponsive polymer composition. In such a case, reservoir 13 and its ingredients are maintained at a temperature lower than the gelation temperature, e.g. LOST, of the hydrogel. In another example, reservoir 13 a comprises a polymer composition, and reservoir 14 comprises a cross-linker and any necessary catalyst(s) for cross-linking of the polymer composition.

A device also is provided, comprising a first reservoir, such as a syringe comprising a solution comprising MNP-loaded cells, such as MNP-loaded ADSCs, and one or more additional reservoirs comprising a hydrogel pre-gel (e.g. a thermoresponsive polymer), or ingredients for preparing a hydrogel pre-gel. The reservoirs are connected in a closed fluid path, such as passageways or tubing, to a mixing chamber comprising an outlet. See, e.g., FIGS. 3A and 3B. The device may be included in a kit that also comprises a catheter for placement of a magnet, with or without the contents of the reservoirs.

EXAMPLES

Example 1

This was performed as a 'proof of concept' study to analyze whether the magnet was able to localize nanoparticle-loaded cells (commercially sourced human ADMSCs (Thermo Fisher Scientific, #R7788110) were cultured essentially as described in Example 9, below) by a strong magnetic field irrespective of gravity—to determine the primary force acting on localization, if any. The study design was to fill two rows of a 24-well plate with half of the rows being the experimental group and the other half the control group. The experimental group consisted of fibrinogen, thrombin and nanoparticle-loaded cells (with a magnet placed on the side of the well plate) while the control group consisted of fibrinogen, thrombin and cells. The fibrin gel was allowed to solidify in a 37° C. incubator with the magnet placed for 30 minutes. After incubation, MTT (3-(4,5-dimethylthiazol-2-yl)-2,5-diphenyltetrazolium bromide) was administered to each well to qualitatively see where the cells were located within each gel. It was found that the nanoparticle-loaded cells localized closer to the magnet while the control group had homogeneous distribution of cells within their respective gels.

Example 2

Figure 3A:
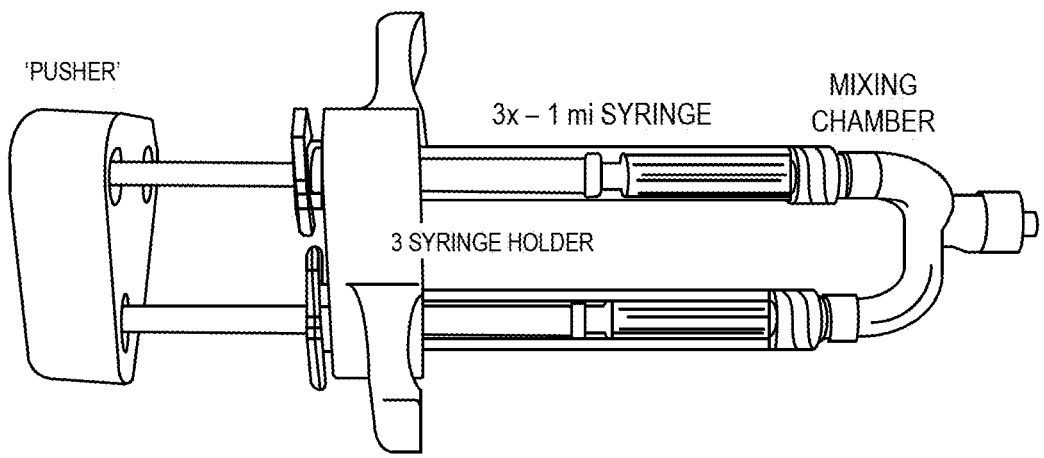
FIGS. 3A and 3B are photographs of two versions of a mixing device for delivery of fibrin gel and nanoparticle-loaded cells, with one syringe body holding fibrinogen, a second holding thrombin, and a third holding nanoparticle-loaded cells.

This was performed as a repeat study of Example 1 to assess a customized 3-syringe mixing chamber device for delivery of the fibrin gel and nanoparticle-loaded cells (see, e.g., FIGS. 3A (with guide pins) and 3B (without guide pins)). It was found that using the mixing chamber device was no different than mixing fibrinogen, thrombin and the cells manually. An MTT assay revealed that the nanoparticle-loaded cells were able to localize towards the magnet while the control group did not exhibit any localization.

Example 3

Figure 4A:
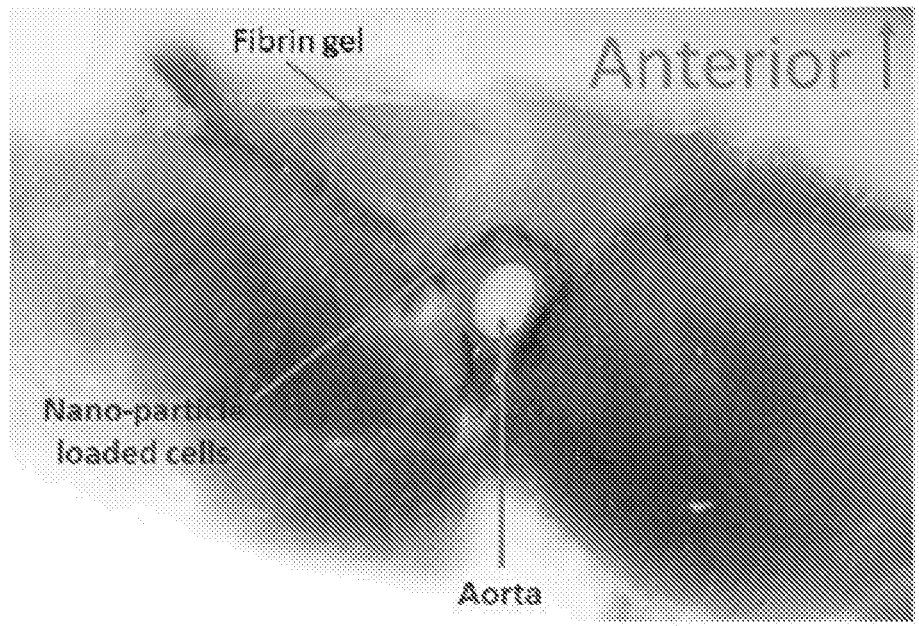
FIGS. 4A and 4B provide photographs of Experimental (FIG. 4A) and Control (FIG. 4B) aortas according to Example 3.
Figure 4B:
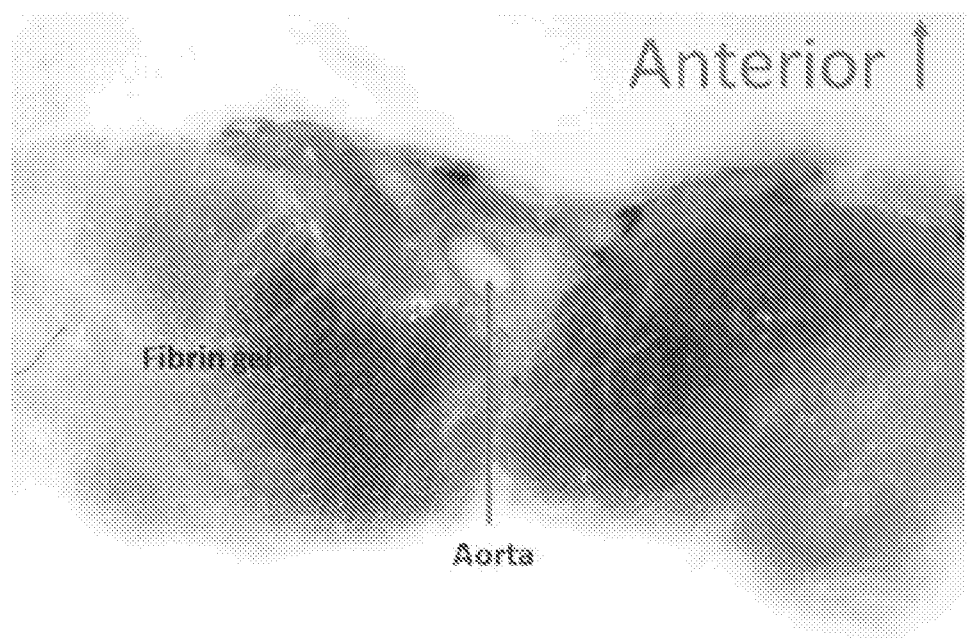
Figure 4C:
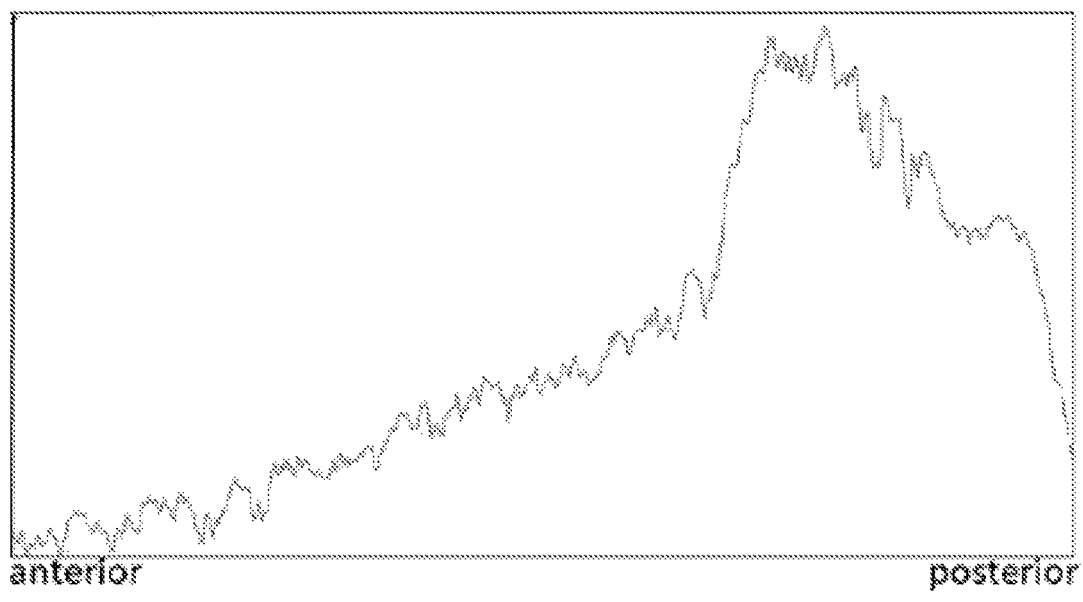
FIG. 4C shows gel quantification (ImageJ) of inverse intensity values of the rectangular region of interest. Rat 03 (FIG. 4A) exhibits a higher peak response near the anterior of the aorta while Rat 04 (FIG. 4B) is more evenly distributed.
Figure 4C:
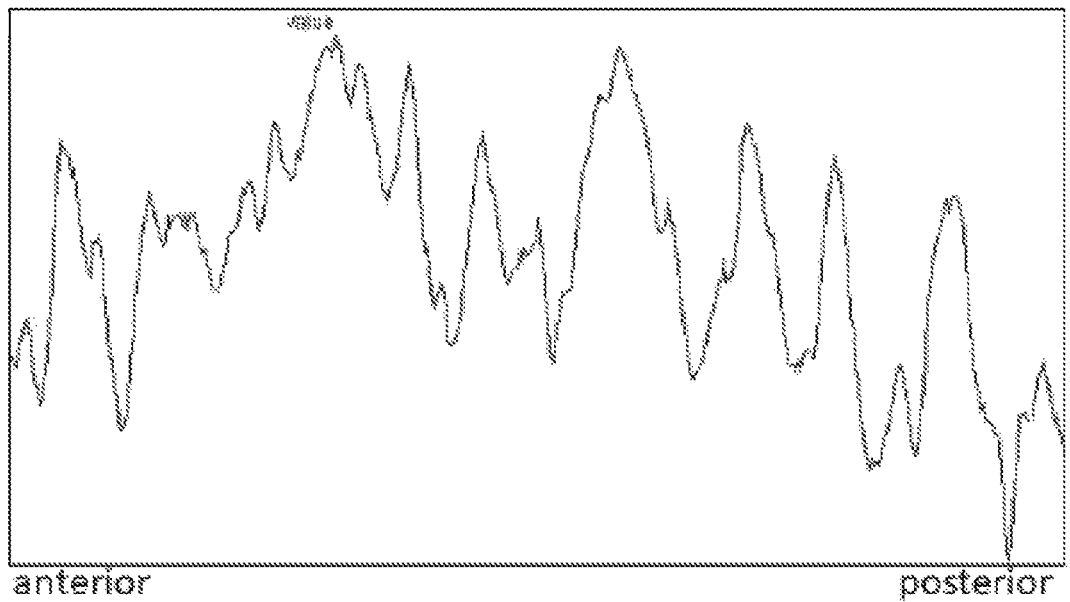

An experiment was performed to understand if the cells were able to localize towards the source of the magnetic field before the fibrin gel hardened. In the proposed clinical treatment method, the stem cells are intended to interact with the diseased tissue while the fibrin gel encapsulates the region of interest. The experiment was performed by injecting the fibrin gel constituents and nanoparticle-loaded human adipose-derived mesenchymal stem cells (ADMSCs), essentially as described in Example 9, below, onto the anterior portion of the abdominal aorta of a sacrificed rat (n=6). The experimental group (n=3) had a magnet placed underneath the rat for 30 minutes while the control group (n=3) did not have a magnet. Sections of the aorta and surrounding tissue were imaged after being stained with DAPI and HNA. It was seen (both qualitatively and quantitatively) that the nanoparticle-loaded cells are on top of the anterior portion of the aorta with encased in fibrin gel while the fibrin gel in the control group has homogeneously distributed cells (See FIGS. 4A-4C).

Example 4

A study was performed to ensure that delivery through a port, silicone catheter and sponge would not hinder delivery to live mice with AAA. A port, silicone catheter and sponge are used to target the abdominal region of the mouse. Successful delivery of the fibrin gel and nanoparticle-loaded stem cells rely on the cells to be drawn towards the magnetic field. Raw chicken wings (n=4) were heated to 37° C. with their radial artery exposed and the sponge was sutured onto the radial artery. A volume of 0.9 ml of the mixture (fibrinogen, thrombin and nanoparticle-loaded cells, essentially as described in Example 9, were injected into the port and delivered to the radial artery with and without the magnet (n=2 control and n=2 experimental). The chicken wings were incubated for an additional 30 minutes before fixing. Preliminary images show that the cells with nanoparticles were drawn towards the radial artery with noted intensity differences between the control and experimental group sponges.

Figure 5A:
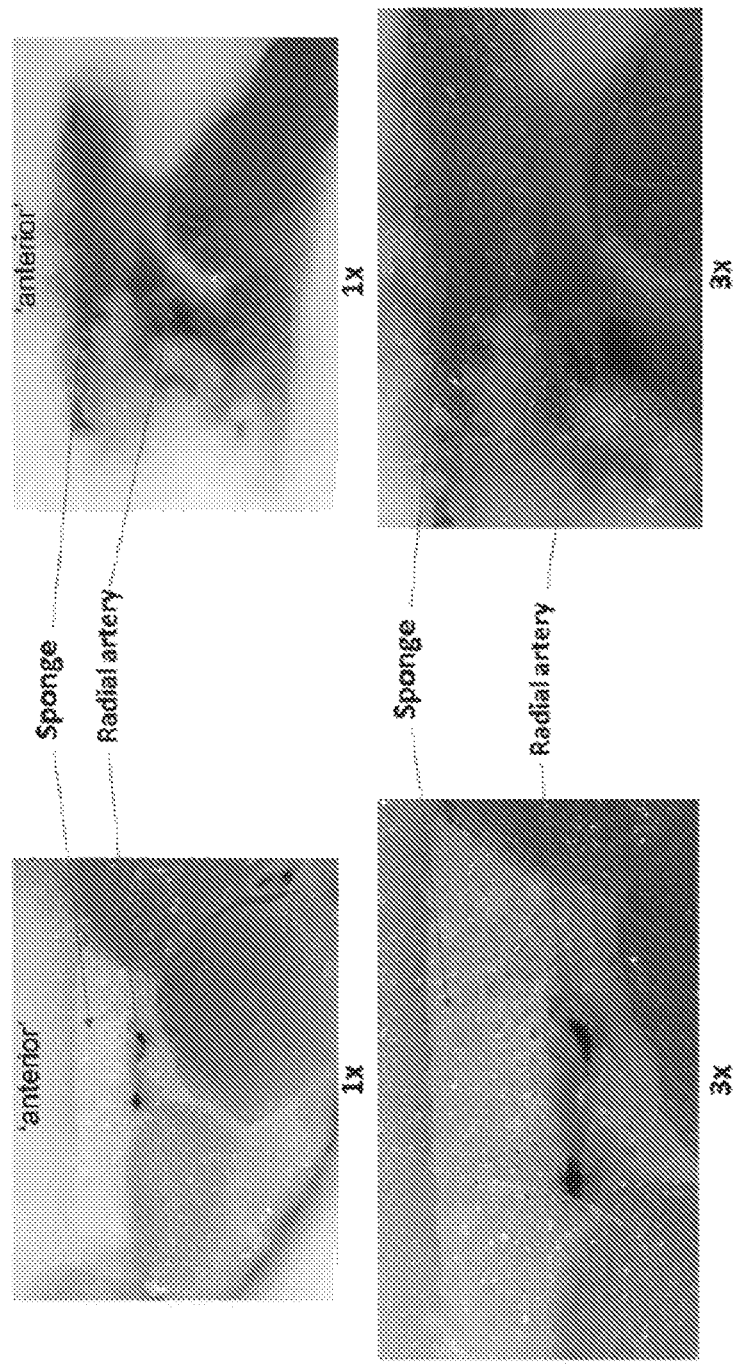
FIG. 5A provides photographs showing the distribution of cells, and FIG. 5B provides photographs (top) and scans (bottom) of nanoparticle-loaded cell distribution, as described in Example 4.
Figure 5B:
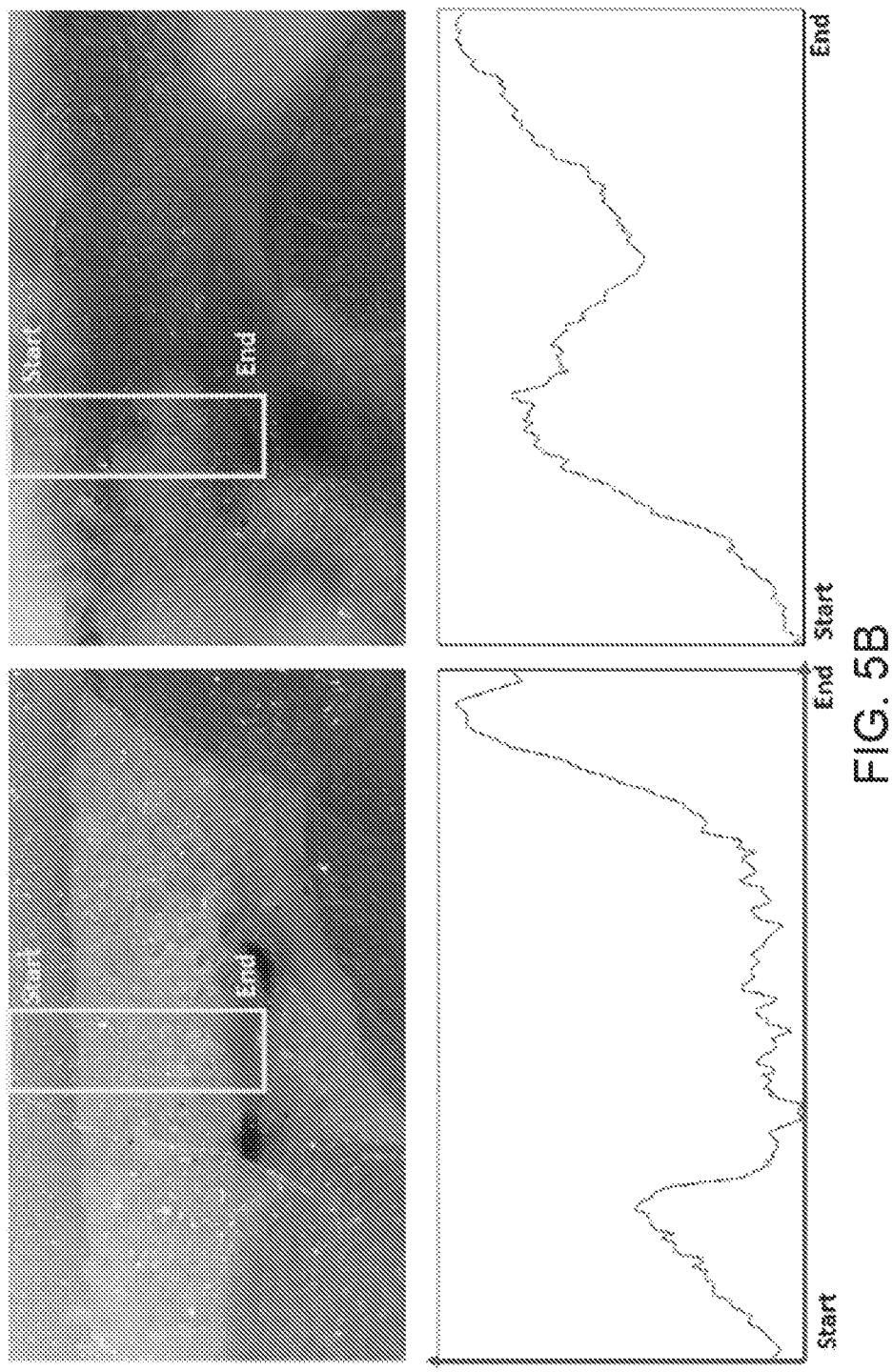

In FIG. 5A, a sponge was placed on top of the radial artery and fibrin gel and nanoparticle-loaded human ADMSCs were delivered through a port and catheter. The left (experimental) had a magnet placed underneath, while the right (control) did not have a magnet. It is seen that the fibrin gel and cells passed through the sponge in the experimental group, while the sponge in the control group retained the fibrin gel and nanoparticle-loaded cells. As seen in FIG. 5B, the sponge from the experimental group (left) has very little pigment within the sponge, while the sponge of the control group (right) has pigment from the nanoparticles. It is unclear from this experiment exactly where the cells were distributed, which can be analyzed more closely in future work.

Example 5

Assesses the port, silicone catheter and sponge delivery to a chicken radial artery placed on top of agarose gel (n=6) in a petri dish. The mixture of fibrin gel and nanoparticle-loaded cells is prepared essentially as described in Example 9, below. The control group consists of the fibrin gel and nanoparticle-loaded cells without a magnet, while the experimental group consists of the fibrin gel, nanoparticle-loaded cells with a magnet placed underneath the agarose gel for 30 minutes. Each petri dish is imaged to determine where the cells are relative to the radial artery and agarose gel.

Example 6

An in vivo experiment is performed with live mice that have been induced with abdominal aortic aneurysm (AAA) with elastase. The mixture of fibrin gel and nanoparticle-loaded cells is prepared essentially as described in Example 9, below. The experimental group consists of mice that have been injected with the fibrin gel, nanoparticle-loaded stem cells with a magnet placed on the posterior of the mouse for 30 minutes (n=6). The control group of mice is injected with fibrin gel and nanoparticle-loaded stem cells without a magnet (n=6). There are to be three time points in which the mice will be harvested after injections: 1 hour (2 control and 2 experimental mice), 3 days (2 control and 2 experimental) and 7 days (2 control and 2 experimental). After the mice are harvested, histology is performed, along with additional imaging. Initial studies were inconclusive due to sectioning artifacts and may be repeated.

Example 7—Delivery to Rat Aorta

Periadventitial delivery of adipose-derived mesenchymal stem cell treatment has demonstrated that abdominal aortic aneurysm progression in a murine elastase-induced model was halted. The localized delivery method required the mice to receive ADMSCs through a subcutaneous port leading to a sponge implanted on the anterior portion of the aorta. In order to test this potential therapy in a large animal model and to promote clinical translation, a minimally-invasive and robust means of localized delivery of the stem cells is needed.

The influence of a neodymium permanent magnet (surface field of ~4100 Gauss) on ADMSCs loaded with iron nanoparticles was determined. Human ADMSCs (Thermo Fisher Scientific, #R7788110) were cultured at 37° C. with adipose-derived stem cell growth medium (Cyagen Biosciences, Inc., CA. USA), with media changes every 2-3 days. Before removing the ADMSCs from their flasks, 200 nanometer iron nanoparticles were included in the final media change and incubated for 24 hours. A custom designed 3D printed mixing apparatus (see, e.g., FIGS. 3A and 3B) was used to inject the fibrinogen (3.7 mg/ml), thrombin (0.21 units/ml) and nanoparticle-loaded ADMSCs (6 ml, $5 \times 10^5$ cells/ml) onto the anterior abdominal aorta of a sacrificed rat that was placed on a stage with (n=3) and without (n=3) a neodymium permanent magnet. The fibrin gel was allowed to set for 30 minutes at 37° C. with the magnet still placed. A large section of the rat anterior abdominal aorta was excised and fixed in paraformaldehyde (PFA) overnight and sectioned. The experimental group (ADMSCs, iron nanoparticles, fibrin and magnet) demonstrated that the cells were localized onto the anterior surface of the aorta while being encapsulated by fibrin gel. The control group (ADMSCs, nanoparticles, fibrin without magnet) revealed a homogeneous distribution of cells within the fibrin gel. Localization of nanoparticle-loaded ADMSCs with a strong permanent magnet was thus demonstrated to be a potential method for cell delivery.

Exemplary features of the method include:
a) Ability to target cells to the surface of specific tissues or organs in the human body through minimally invasive means.
b) A magnetic field draws therapeutic cells to targeted surface where they are fixed in place with a hydrogel.
c) A multi-syringe injection device allows simultaneous mixing of hydrogel components and therapeutic cells for immediate treatment delivery.

Example 8—Delivery to Pig Aorta

Figure 6:
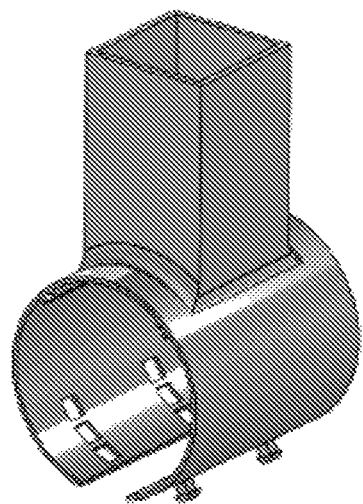
FIG. 6 is an elevated view of an exemplary 3D-printed fibrin gel holder.

A diametric magnet (having a diameter of 6.35 mm, a length of 25 mm, and a pull radius of 3 cm) was used to attract nanoparticle-loaded cells, prepared essentially as described in Example 9, below, in vitro to adventitial tissue of a pig aorta. The diametric magnet was placed inside the lumen of the pig aorta at the end of a perfusion rod. The nanoparticle-loaded ADMSCs were prepared essentially as described in Example 9, below. Aortas were harvested from 6 adult pigs and subsequently frozen in Hank's Balanced Salt Solution. The average aortic diameter was 1.8 cm. The aortas were prepared by removing connective tissue and ligating any branch arteries. Aortas were fixed to a custom-built perfusion system, lined with latex to allow for pressurization, and subjected to pulsatile loading at 0.5 Hz using saline. The perfusion system achieves "human-like" conditions with a heart rate of roughly 60 bpm (beats per minute), pressure pulses ranging from 70-130 mmHg, and a fluid temperature of 37° C. A custom 3D-printed fibrin gel holder (FIG. 6) was manufactured to hold 3 mL of fibrin gel with cells loaded with iron nanoparticles, essentially as described in Example 9. The control group consisted of three pig aortas without the presence of a magnet with the fibrin gel and iron nanoparticle-loaded cell mixture placed into the custom 3D-printed fibrin holder.

Figure 7:
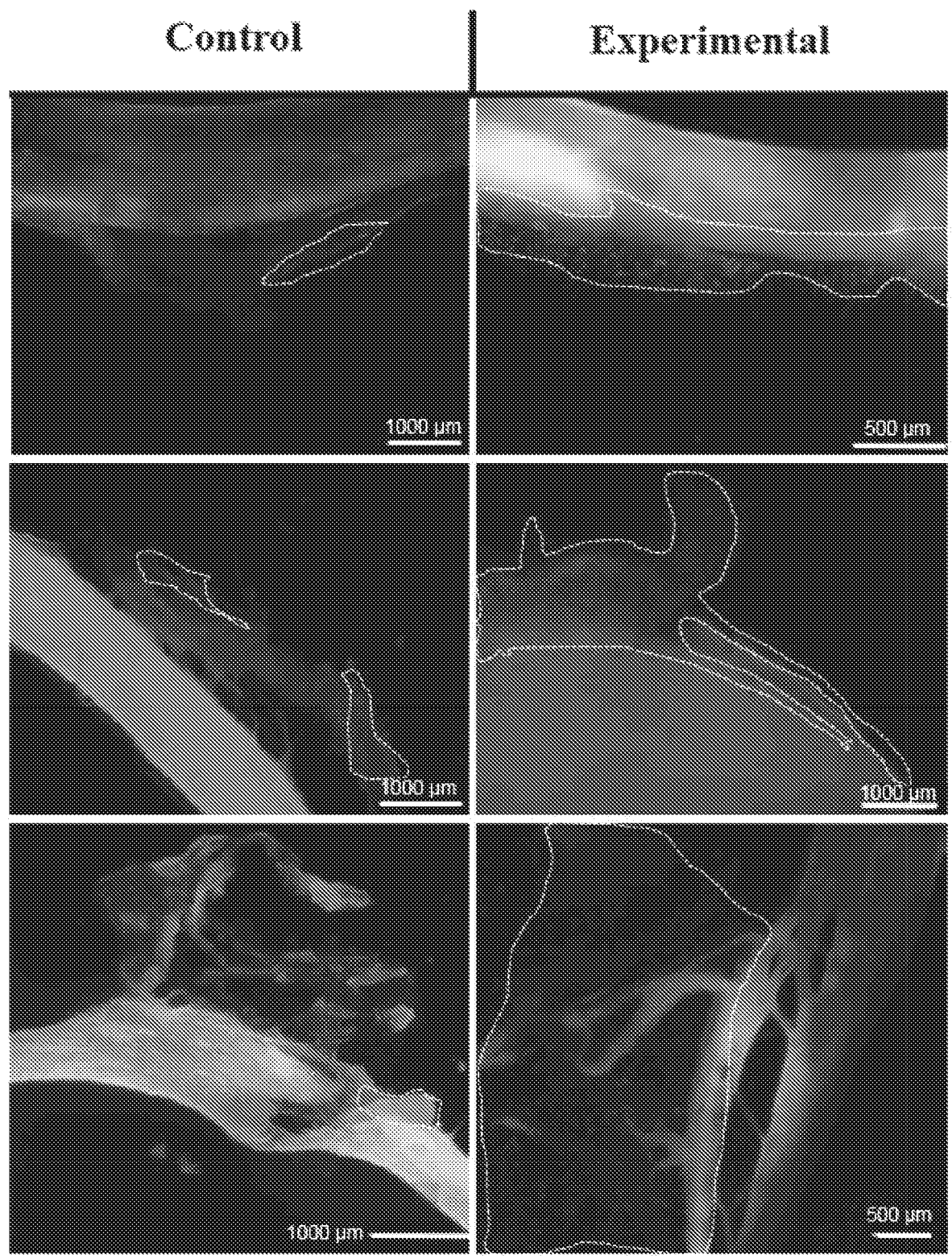
FIG. 7. Pig aorta with and without the presence of a diametric magnet. Cells are dyed with Celltracker and are visualized in the red channel (red-orange portions in original are encircled with a dotted line).

The day of the experiment, cells were loaded into the hydrogel, deposited onto the aorta+gel holder under pulsation, and left for 15-20 minutes to allow for curing. The section around the gel holder was excised and left in the 37° C. incubator for 30-45 minutes for further curing, then fixed overnight in 0.37 wt % paraformaldehyde. The next day, they were cryosectioned and stored in the freezer for imaging. The experimental group consisted of three pig aortas with the presence of a magnet Results are seen in FIG. 7. The original for FIG. 7 is in color and the experimental group shows significantly more robust red coloring and significantly larger red-colored areas as compared to the controls).

Example 9—Tuning of Delivery Parameters

Cell culture. Commercially sourced human ADMSCs (Thermo Fisher Scientific, #R7788110) were cultured in 75-cm$^2$ or 175-cm$^2$ tissue culture flasks (Corning) and grown under defined culture media [1:1 Dulbecco's modified Eagle's medium (DMEM; Gibco #11965) to DMEM/F12 (Gibco #113300) with 10% fetal bovine serum (Atlanta Biologics #S11550), antibiotics (1% Pen/Strep, 0.5% Fungizone, 0.1% Gentamycin), and 10 μL of 10 mM dexamethasone] mixed with 25% Preadipocyte Growth Medium (#C-27410, #C-39425; PromoCell). Culture media was changed every 2-3 days, and when ADMSCs were expanded to near confluence, they were passage expanded utilizing 0.25% trypsin-EDTA (#25200-056; Gibco) or utilized for subsequent experimentation. Cells were used between passages 6-10.

Iron Nanoparticle Loading Efficiency. Cell loading with iron nanoparticles (fluidMAG-D, Chemicell) was performed as follows. Briefly, ADMSCs were incubated overnight with 0.5 mg/mL nanoparticles (100 or 200 nm diameter) in growth medium. Cells were also loaded with a 0.25 mg/mL and 1.00 mg/mL iron nanoparticles, and loading efficiency was calculated as the total number of cells containing iron nanoparticles (identified by staining described below) per view divided by the total number of cells per view (n=3 per group, 3 images per n).

Fibrin Gel Fabrication. All experiments using ADMSC-seeded fibrin constructs were fabricated by mixing bovine fibrinogen type I (3 mg/mL or 10 mg/mL, Sigma-Aldrich, St. Louis MO) with bovine thrombin (1 NIHU/mL, Sigma-Aldrich, St. Louis, MO) and ADMSC cell suspension (5.0× 10$^4$ cells/gel, 1.0×10$^5$ cells/gel, and 2.0×10$^5$ cells/gel). The gels were plated within 24-well plates (Corning). Gels were either allowed to polymerize for at least 2 hours in incubator conditions (37° C., 5% $CO_2$) or handled immediately before adding ADMSC culture media for the viability and migration assays (see, below). The gels were then cultured in incubator conditions according to the treatment condition.

Cell Viability. In order to determine the optimal fibrin gelation parameters for ADMSC viability, the ADMSC viability of ADMSC-seeded fibrin constructs was evaluated using an MTT assay. After 5 days in culture, 200 mL of serum-free α-MEM and 20 mL of Thyazolyl Blue Tetrazolium Bromide (Sigma-Aldrich, St. Louis, MO) was added to each sample. Samples were then incubated at 37° C. for four hours to allow crystal formation. The supernatant volume was then carefully removed and 200 μL of 0.04N HCl in 2-propanol solution was added to dissolve the crystals. Samples were kept in the dark at 4° C. for 24 hours. Lastly, absorbance readings were taken for 100 μL of the solution for each condition at 550 nm wavelength using a microplate reader (BioTek, Winooski, VT). The final number of cells was calculated using a standard curve generated for known cell concentrations.

Figure 8:
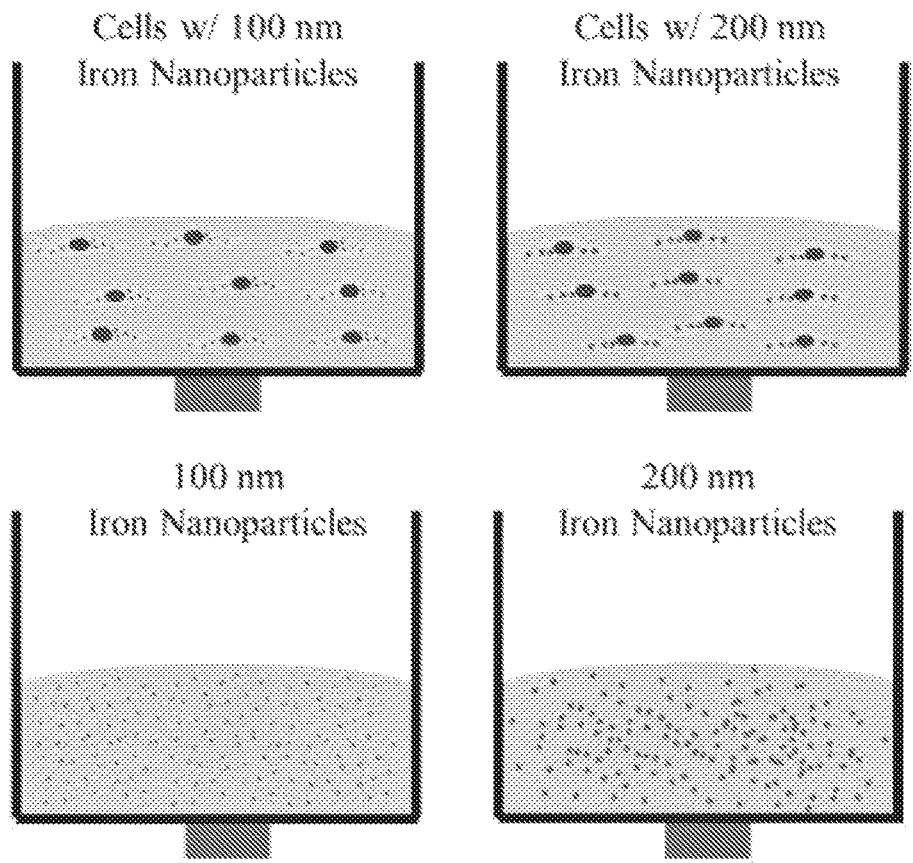
FIG. 8 is a schematic depicting experimental groups as described in Example 9.

Magnetic Migration. In order to determine the localization effects of short-term magnetic stimulation, ADMSCs were loaded with iron nanoparticles (100 and 200 nm diameter) and seeded in a fibrin gel. Fibrin gels were also formed with iron nanoparticles only (100 and 200 nm diameter). The gels were plated in a 24-well plate. A magnet (0.3T) was placed under the 24-well plate in the center of each well. In order to determine the temporal effects of magnetic stimulation of an actively gelling construct, a magnet was put in place at three different time points: at the beginning of gelation (prior to gel plating), mid gelation (20 seconds after gel plating), and after complete gelation (10 minutes after gel plating). Gels were also plated without magnet placement as a control. A side view schematic of the experimental groups is shown in FIG. 8. The gels were cultured in incubator conditions (37° C., 5% $CO_2$) for 24 hours. The gels were then imaged from above to qualitatively assess the localization of the iron nanoparticles.

In order to determine the localization effects of long-term magnetic stimulation, gels made from cells loaded with 200 nm iron nanoparticles and magnet placement at mid gelation were cultured for 5 days. We added an additional magnet size to the longer-term culture experiments. The larger magnet had a greater pull strength (12 lbs. vs. 4 oz.), but the same magnetic field surface strength (0.3 T).

Magnetic Probe Ultrasound Identification. A magnetic probe prototype comprising a magnet within a catheter sheath was imaged within a tissue mimic using a 21 MHz ultrasound linear probe (MS 250) connected to a high frequency imaging system (Vevo2100, Visualsonics, Canada) in B-scan mode. The tissue mimic was made from a 2% gelatin solution contained within a Plexiglas chamber with a clear PVC tube running the length of the chamber to serve as an aorta mimic. The tube was approximately 3 inches from the top of the tissue mimic. Ultrasound images of the aorta mimic were captured with and without the magnetic probe in place and processed to highlight the magnetic probe.

Histology and Imaging. All samples collected for imaging were fixed in 4% paraformaldehyde, frozen, and sectioned. Sections were stained with Prussian Blue stain for iron and DAPI to show nuclei. Images of sections were taken looking at the z-radial plane and taken from the middle of the gel. All sectioned samples were imaged using NIS Elements software (version 4.0).

Figure 9:
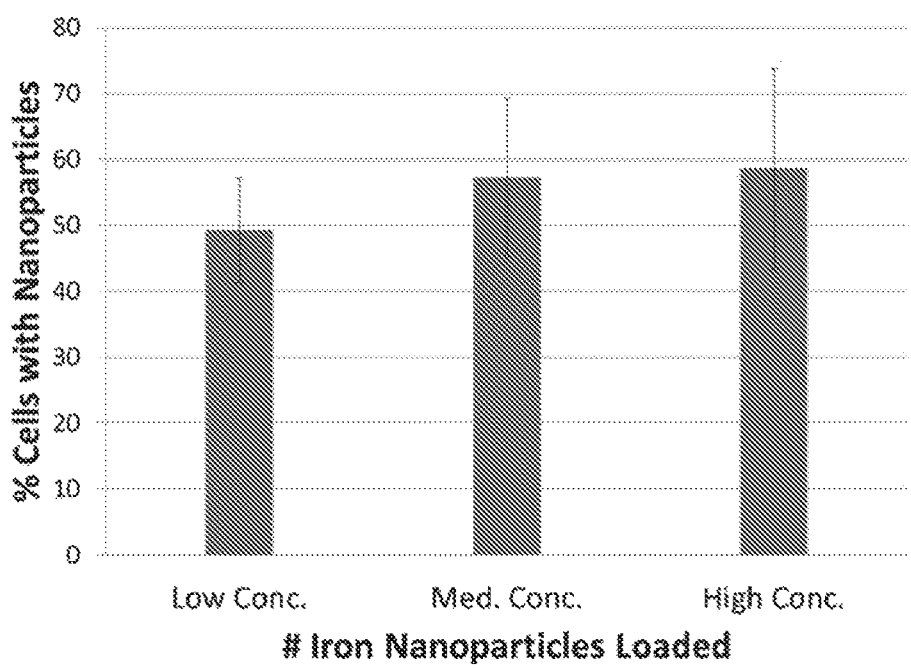
FIG. 9. Iron nanoparticles load at the same efficiency at all tested iron nanoparticle concentrations. The percentage of cells staining positive for iron nanoparticles was 49.3±7.9, 57.2±11.9, 58.6±15.2 (mean±SD) for the low (0.25 mg/mL), medium (0.50 mg/mL), and high (1.00 mg/mL) concentration of iron nanoparticles, respectively. The percentage of cells with positive staining for iron nanoparticles is shown on the y-axis. The iron nanoparticle concentration groups are labeled on the x-axis.
Figure 10:
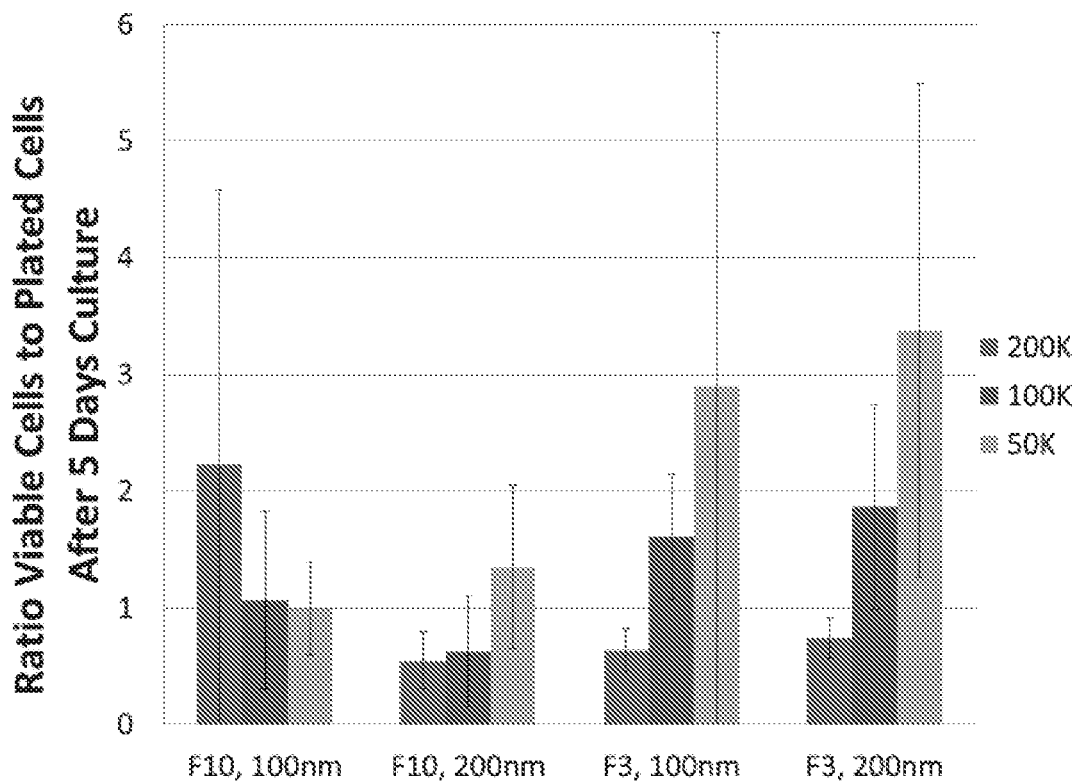
FIG. 10. Fibrinogen concentration, starting cell number and a mixed effect term of fibrinogen concentration and starting cell number are significant predictors of ratio of viable cells to plated cells after 5 days in culture. The ratio of viable cells to plated cells after 5 days in culture is shown on the y-axis. The fibrinogen concentration (F3=3 mg/mL, F10=10 mg/mL) and iron nanoparticle size groups are labeled on the x-axis. The starting cell number is labeled with gray ($2.0\times10^5$), dark gray ($1.0\times10^5$) and light gray ($5.0\times10^4$).
Figure 11:
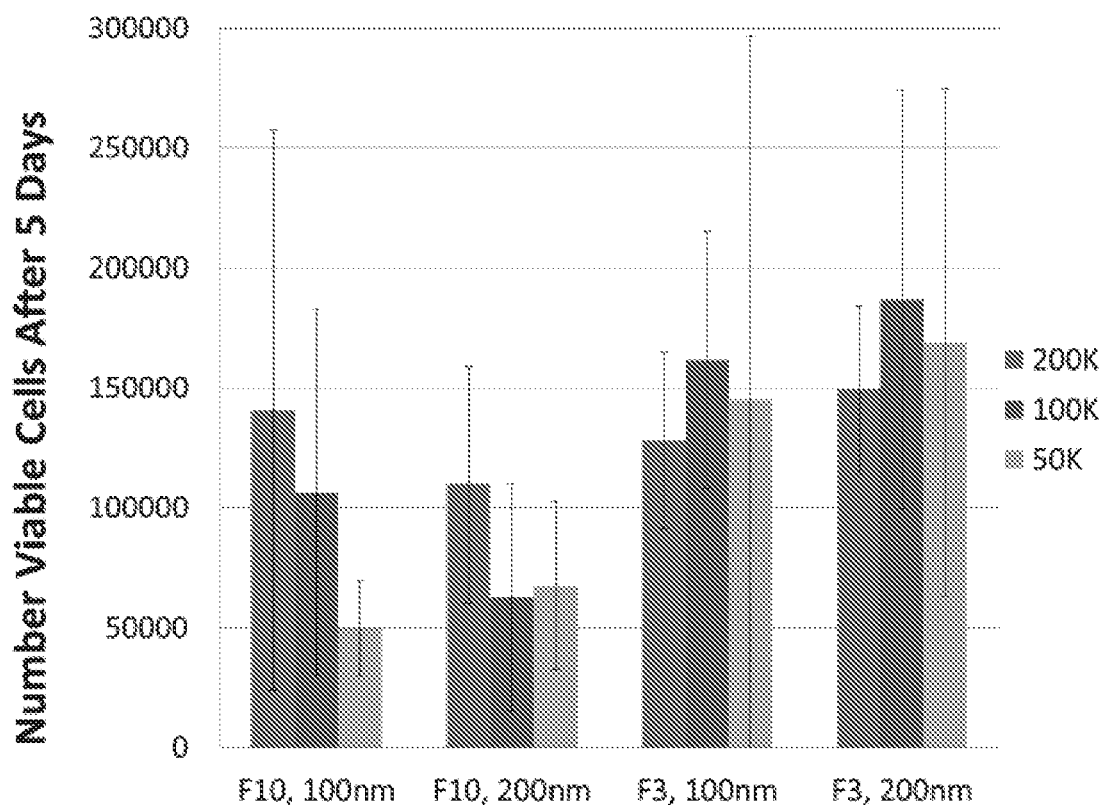
FIG. 11. Fibrinogen concentration is a significant predictor of number of viable cells after 5 days in culture. The number of viable cells after 5 days in culture is shown on the y-axis. The fibrinogen concentration (F3=3 mg/mL, F10=10 mg/mL) and iron nanoparticle size groups are labeled on the x-axis. The starting cell number is labeled with gray ($2.0\times10^5$), dark gray ($1.0\times10^5$) and light gray ($5.0\times10^4$).

Statistics. A linear regression model was used to determine significant predictors for the cell viability experiments.
Results Optimal Iron Nanoparticle and Fibrin Gel Parameters. When preforming the iron nanoparticle loading efficiency experiments, we found that ~52% of cells had iron nanoparticles (FIG. 9), and a one-way ANOVA revealed that the tested concentrations of iron nanoparticles had no effect on loading efficiency (p=0.495). A linear egression revealed that fibrinogen concentration (p<0.001), starting cell number (p<0.001), and a mixed effect term of fibrinogen concentration and starting cell number (p=0.006) to be significant predictors of the ratio of viable cells to initial cells plated. These results are shown in FIG. 10. Lower fibrinogen and plated cell concentrations lead to higher ratios of viable cells to initial cells plated. However, only fibrinogen concentration is a significant predictor (p<0.001) of total number of cells after 5 days in culture (FIG. 11).

Figure 12:
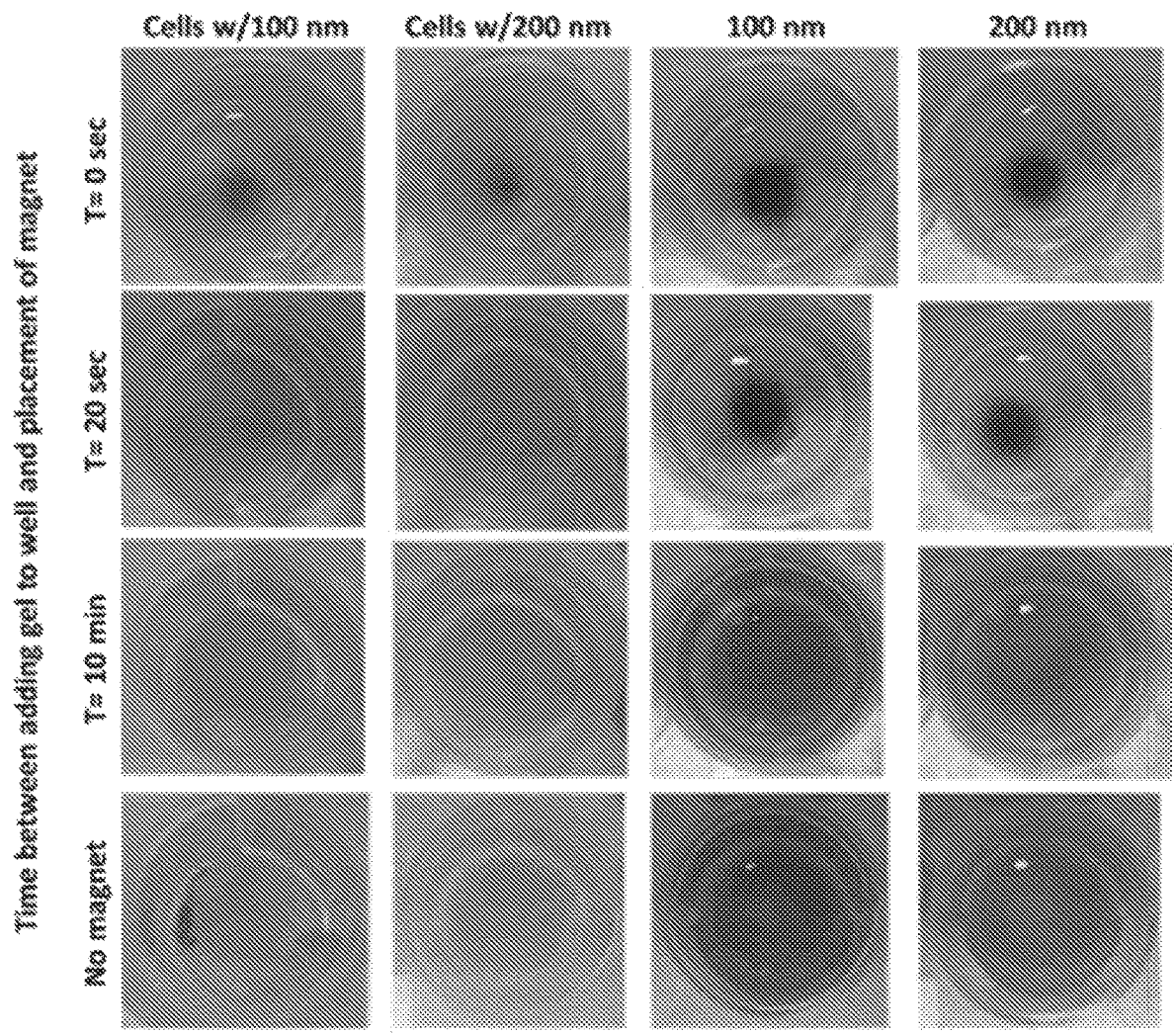
FIG. 12. The attractive force between iron nanoparticle and magnets can move cells and iron nanoparticles through a fibrin gel before gelation is complete. Iron nanoparticles appear brown within a fibrin gel 24 hours after plating. Columns are labeled with experimental group. Rows are labeled with time of magnet placement with respect to plating.

In-vitro Magnetic Force Induced Cell Localization. The ability of magnetic attractive forces between a magnet and iron nanoparticles to move cells through a fibrin hydrogel was assessed. This ability was tested in short-term and long-term studies. The results of the short-term study are shown in FIG. 12. Cells loaded with iron nanoparticles were unable to be pulled through a fibrin hydrogel when the localizing magnetic field was introduced 20 seconds after plating the gel. This was not the case in the experimental group that did not include cells as iron nanoparticles were still able to localize over the magnet at the 20 second time point but were unable to localize at the 10-minute time point. Though the pictures shown in FIG. 37 were taken one day after plating the gels, all groups looked the same shortly after placement of the magnet.

Figure 13:
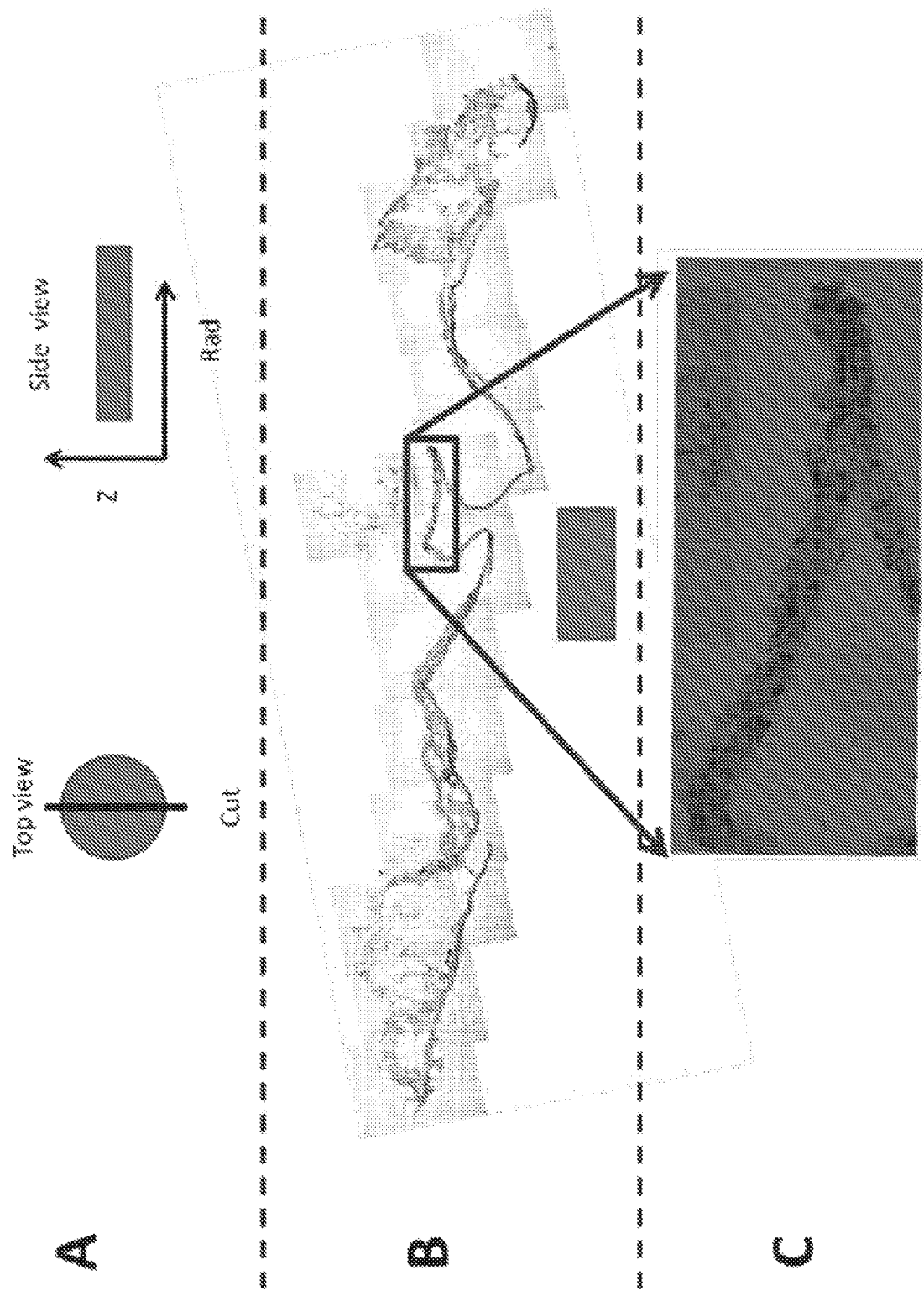
FIG. 13. ADMSCs loaded with iron nanoparticles localize towards a small magnet after five days in culture. A) Schematic of how circular gels were sectioned and imaged. The circular gel was cut in half, and then sections were made across the z-radial plane. B) The gel has been stained with Prussian Blue dye to identify iron nanoparticles. The lower rectangle represents the relative position and size of the magnet to the gel during culture. The rectangular box is the area that is magnified in panel C which shows the DAPI and Prussian Blue stain merged.

Because acute magnetic exposure was unable to localize the cells within the fibrin hydrogel, it was determined whether long term magnetic exposure could accomplish the task. When exposed to a magnetic field for five days in culture, cells loaded with iron nanoparticles localized over the source of the magnetic field. FIG. 13 (B) shows a cross section (FIG. 13 (A)) of a fibrin gel exposed to a small diameter magnet for five days that has been stained with Prussian Blue and DAPI. There is compression of the fibrin gel in the area directly over the magnet. FIG. 13 (C) shows a blowup of the rectangle in FIG. 13 (B) for the Prussian Blue stain, DAPI and merged channels from top to bottom respectively.

Figure 14:
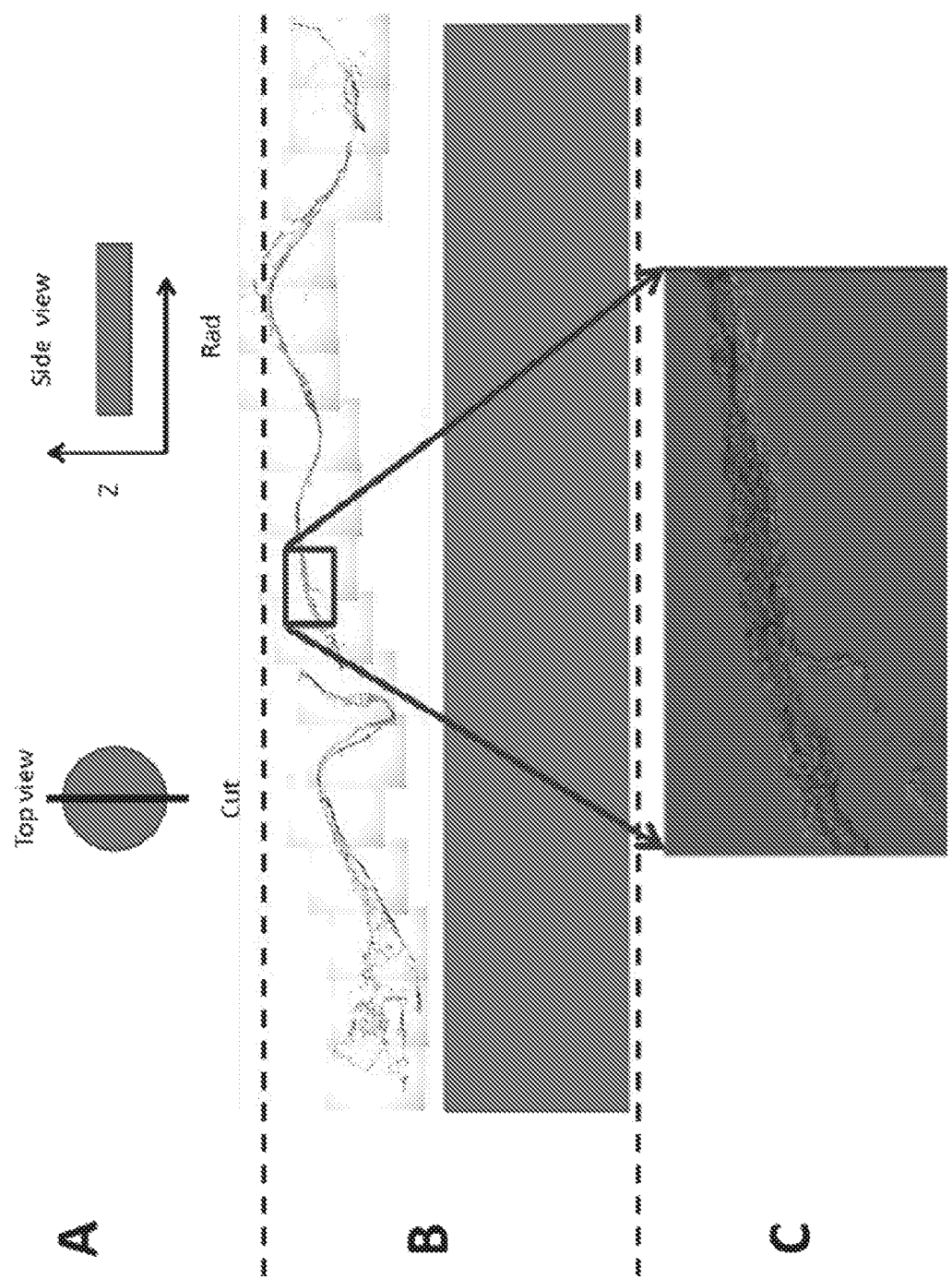
FIG. 14. ADMSCs loaded with iron nanoparticles localize towards a large magnet after five days in culture. A) Schematic of how circular gels were sectioned and imaged. The circular gel was cut in half, and then sections were made across the z-radial plane. B) The gel has been stained with Prussian Blue dye to identify iron nanoparticles. The lower blue rectangle represents the relative position of the magnet to the gel during culture. The rectangular box is the area that is magnified in panel C which shows the DAPI and Prussian Blue stain merged.

FIG. 14 (B) shows a cross section of a fibrin gel exposed to a large diameter magnet for five days that has been stained with Prussian Blue and DAPI. There is a compression of the fibrin gel over nearly the entire gel which is approximately the same size as the large magnet. FIG. 14 (C) shows a blowup of the rectangle in FIG. 14 (B) for the merged Prussian Blue and DAPI channels.

Figure 15:
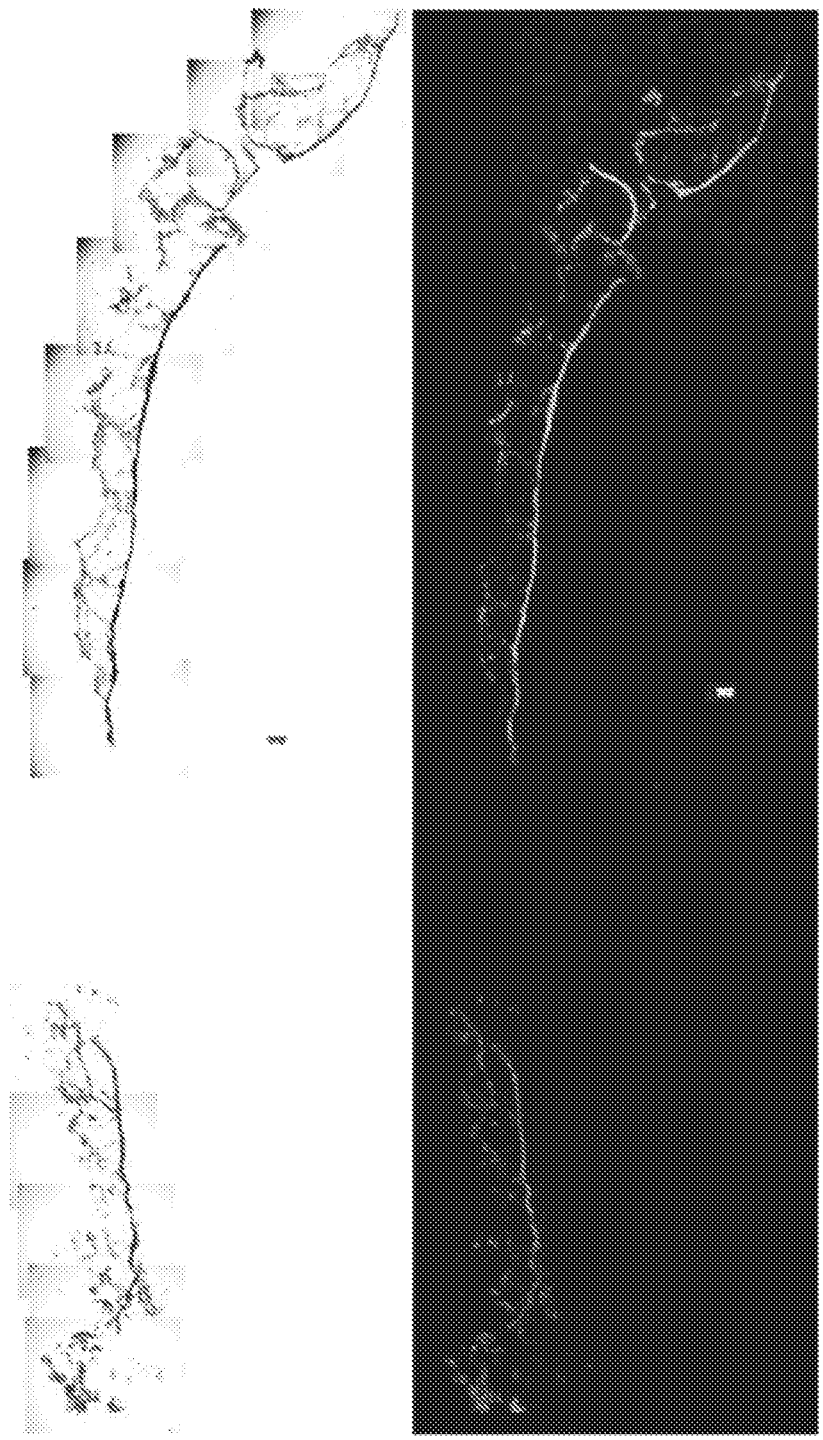
FIG. 15. ADMSCs loaded with iron nanoparticles accumulate at the bottom of the wells after five days in culture. Prussian Blue and DAPI are shown in top and bottom pictures, respectively for the ADMSC iron nanoparticle loaded gel cultured without a magnet in place.
Figure 16:
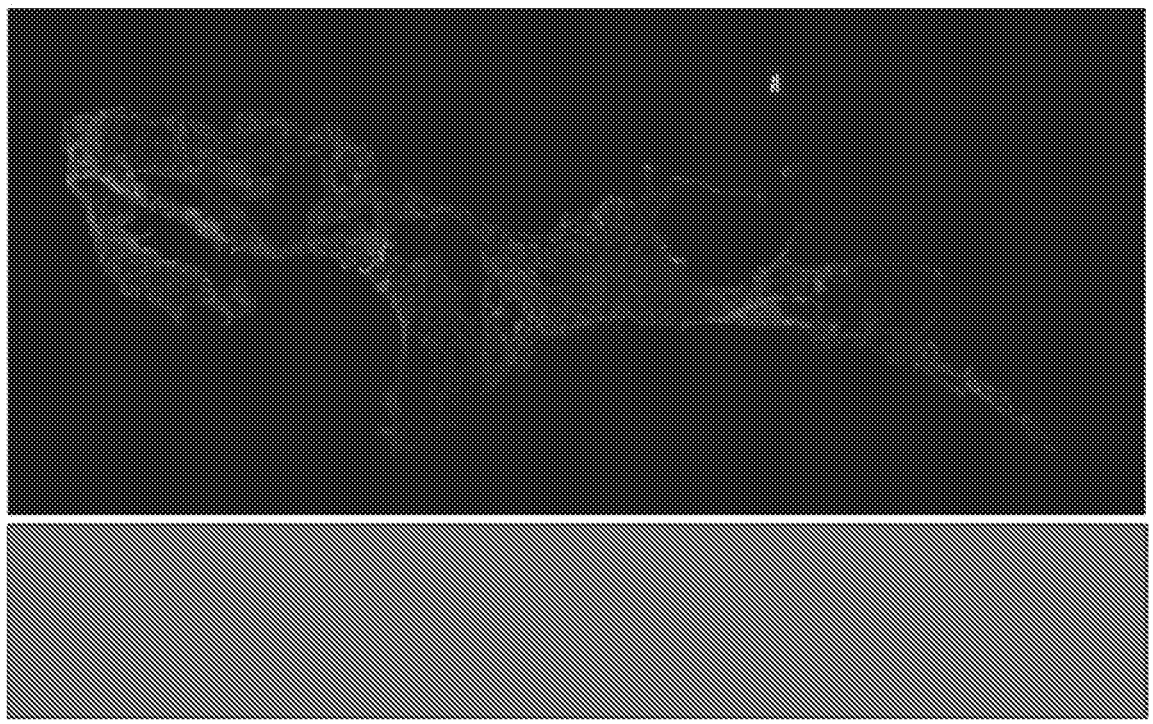
FIG. 16. ADMSCs without iron nanoparticles remain dispersed throughout the gel after five days in culture. DAPI stain for ADMSCs without iron nanoparticles when cultured for five days with a large magnet in place. The lower rectangle represents the relative position and size of the magnet to the gel during culture.
Figure 17:
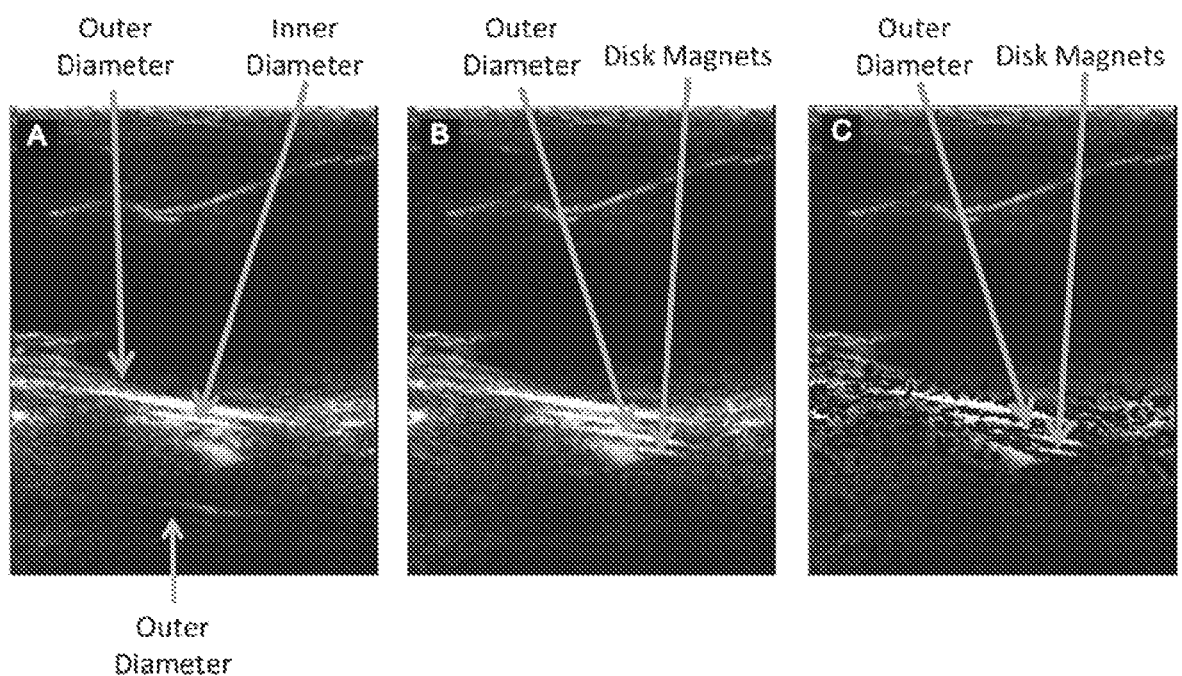
FIG. 17. Ultrasound images showing that the magnetic probe is visible within tissue and aorta mimics using ultrasonic imaging. A) An ultrasonic image shows the aorta mimic within the tissue mimic. B) An ultrasonic image shows the magnetic probe within the aorta mimic. C) The same ultrasonic image from panel B is shown with the changes from panel A highlighted in red (in original).

FIG. 15 shows a Prussian Blue and DAPI stain of an ADMSC seeded gel loaded with iron nanoparticles that was cultured for 5 days without any magnet in place. There is a small accumulation of cells along the bottom of the gel, but the gel remains thicker than the counterparts shown in FIG. 13 & FIG. 14. FIG. 16 shows a DAPI stain of an ADMSC seeded gel that had not been loaded with iron nanoparticles. The gel was cultured for 5 days with the large magnet in place. The gel is thicker and less dense in appearance compared to the iron nanoparticle loaded counterpart in FIG. 14. Magnetic Probe Ultrasound Identification. The ultrasonic images of the magnetic probe are shown in FIG. 17. In FIG. 17 (A) the image was captured without the magnetic probe in place, and the anterior aortic mimic outer and inner diameters can be seen in the image. The posterior outer diameter can also be seen. In FIG. 17 (B), the magnetic probe was brought into the field of view, and the anterior portion of the catheter and the magnets can be seen. The magnetic probe is highlighted in FIG. 17 (C).

In sum, no statistical difference in iron nanoparticle loading efficiency was observed among the tested concentrations. Loading efficiency is expected to depend on cell type. Total cell number and ratio of cells after five days in culture to plated cells were not dependent on the size of iron nanoparticle used.

Figure 3B:
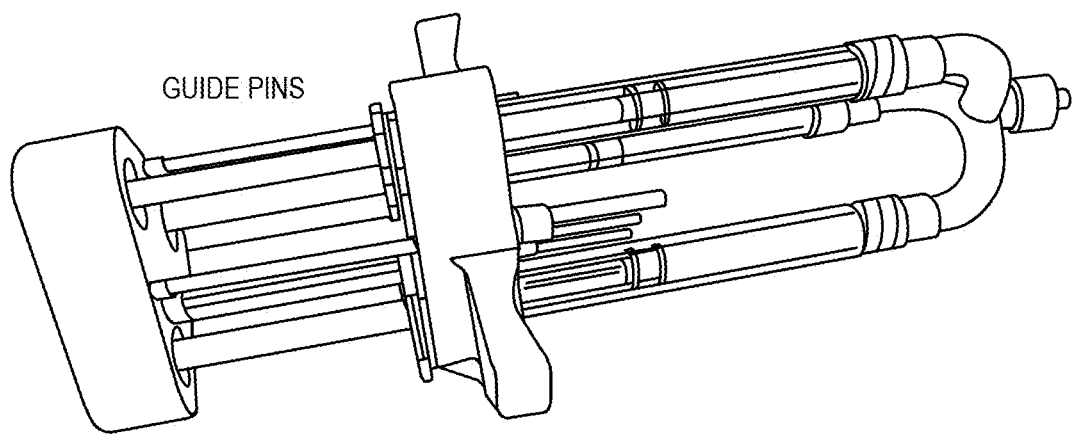

In additional studies, use of a custom mixing device similar to the device of FIGS. 3A and 3B, for mixing and delivering the cell-containing pre-gel material provided a suitable degree of mixing comparable to manual mixing. Further, ultrasound localization of magnets relative to a blood vessel was evaluated in an in vitro model and proved to be an adequate method for visualization of the location of the magnet.

Viability experiments did show fibrinogen concentration to be a significant predictor of both total cell number and ratio of cells after five days in culture to plated cells. Starting cell concentration and a cross talk term between starting cell concentration and fibrinogen concentration were also significant predictors of ratio of cells after five days in culture to plated cells. This knowledge can also be used to manipulate a potential cell therapy. The fibrinogen concentration should be kept high if cell division is undesired. Conversely, if cell division is desired, then fibrinogen and starting cell concentration should be kept low. In the present system, cell division is undesirable since a goal is to have ADMSCs producing the growth factor profile shown at confluence. However, a lower fibrinogen concentration was desirable so that the cells can more easily move towards the magnet. A compromise for the present use would be using a high cell concentration with a low fibrinogen concentration.

Using the combination of fibrin gels and iron nanoparticles seem to have no negative effects on the therapeutic ADMSCs in terms of viability. ADMSCs loaded with iron nanoparticles contained in a fibrin gel will move through the fibrin gel solution to a magnetic field source if the fibrin has not completely gelled.

Long term experiments show that ADMSCs loaded with iron nanoparticles contained in a fibrin gel will move to a magnetic field source even after the fibrin has gelled to an appreciable amount. The movement in the long-term experiments seems to be due to compression of the fibrin gel rather than movement of the cells through the gel. This is apparent in FIG. 13 & FIG. 14 which shows compacted gels directly over the external magnet while FIG. 16 shows that ADMSCs without iron nanoparticles within a fibrin gel do not compact over an external magnet.

The present invention has been described with reference to certain exemplary embodiments. However, it will be recognized by those of ordinary skill in the art that various substitutions, modifications, or combinations of any of the exemplary embodiments may be made without departing from the spirit and scope of the invention. Thus, the invention is not limited by the description of the exemplary embodiments.

What is claimed is:

1. A method of delivering a cell to an aortic aneurysm, comprising:
   mixing cells comprising internalized magnetic particles with a hydrogel pre-gel composition;
   depositing the pre-gel composition comprising the cells at a site on or adjacent to a tissue, under conditions suitable for gelation of the pre-gel composition such that the pre-gel composition forms a hydrogel at the site; and
   prior or during gelation of the hydrogel, applying a magnetic field to the cells in the deposited pre-gel to draw the cells to the aneurysm.

2. The method of claim 1, wherein the cells are targeted to adventitia in the aneurysm.

3. The method of claim 1, wherein the pre-gel composition comprises a thermoresponsive polymer composition and forms a hydrogel at 37° C.

4. The method of claim 1, wherein one or more compounds or compositions in the pre-gel composition undergoes a chemical reaction to produce the hydrogel.

5. The method of claim 4, wherein the pre-gel composition comprises thrombin and fibrinogen.

6. The method of claim 5, wherein the pre-gel composition comprises from 0.1 mg/mL to 15 mg/mL fibrinogen.

7. The method of claim 1, wherein the cell is a pluripotent cell, a stem cell, a multipotent cell, or a progenitor cell.

8. The method of claim 1, wherein the cell is a mesenchymal stem cell.

9. The method of claim 1, wherein the magnetic particles are ferromagnetic nanoparticles having a diameter ranging from 1 nm to 500 nm.

10. The method of claim 1, further comprising adding the magnetic particles to cell culture media comprising cells and culturing the cells with the magnetic particles to produce the cells comprising internalized magnetic particles.

11. A method of treating an abdominal aortic aneurysm, in a patient, comprising delivering mesenchymal stem cells (MSCs) to adventitia on or about the aneurysm by depositing a pre-gel composition comprising MSCs comprising internalized magnetic particles at a site on or adjacent to a tissue, under conditions suitable for gelation of the pre-gel composition such that the pre-gel composition forms a hydrogel at the site; and prior to or during gelation of the hydrogel, applying a magnetic field to the cells in the deposited pre-gel to draw the cells to the tissue.

12. The method of claim 11, wherein the MSCs are adipose-derived mesenchymal stem cells.

13. The method of claim 11, wherein the patient is human.

14. The method of claim 11, further comprising, prior to depositing the pre-gel composition comprising MSCs comprising internalized magnetic particles at a site on or adjacent to the tissue, mixing MSCs comprising internalized magnetic particles with a hydrogel pre-gel composition to produce the pre-gel composition comprising MSCs comprising internalized magnetic particles.

15. The method of claim 11, wherein the pre-gel comprises fibrinogen and thrombin.

* * * * *